(12) United States Patent
Motoyama et al.

(10) Patent No.: US 10,709,348 B2
(45) Date of Patent: Jul. 14, 2020

(54) STANDING MOTION ASSIST DEVICE, STANDING MOTION ASSIST METHOD, AND RECORDING MEDIUM

(71) Applicant: Panasonic Intellectual Property Management Co., Ltd., Osaka (JP)

(72) Inventors: Hiroyuki Motoyama, Shiga (JP); Tsuyoshi Inoue, Nara (JP); Yusuke Kato, Chiba (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 509 days.

(21) Appl. No.: 15/685,138

(22) Filed: Aug. 24, 2017

(65) Prior Publication Data
US 2018/0064357 A1    Mar. 8, 2018

(30) Foreign Application Priority Data
Sep. 2, 2016  (JP) .................. 2016-172299

(51) Int. Cl.
*A61G 5/14*    (2006.01)
*A61B 5/04*    (2006.01)
(Continued)

(52) U.S. Cl.
CPC ........ *A61B 5/04012* (2013.01); *A61B 5/1116* (2013.01); *A61B 5/6812* (2013.01);
(Continued)

(58) Field of Classification Search
CPC . A61B 5/04012; A61B 5/1116; A61B 5/6812; A61B 5/0488; A61H 1/02;
(Continued)

(56) References Cited

U.S. PATENT DOCUMENTS

2010/0094188 A1 *  4/2010  Goffer ................... B25J 9/0006
                                                    602/23
2010/0271051 A1 * 10/2010  Sankai .................. A61H 3/008
                                                    324/679

FOREIGN PATENT DOCUMENTS

JP    2010-253048        11/2010
JP    2010253048 A   * 11/2010  ............... A61G 5/00

* cited by examiner

*Primary Examiner* — Suba Ganesan
*Assistant Examiner* — Aren Patel
(74) *Attorney, Agent, or Firm* — Wenderoth, Lind & Ponack, L.L.P.

(57) ABSTRACT

A standing motion assist device includes a support mechanism attached to a leg of a user to assist the user with motion, a sensor including first and/or second sensors that measure and output posture information and myoelectric potentials of the user, respectively, the sensor outputting measurement data including first measurement data measured after a sitting motion of the user sitting in a chair starts and second measurement data measured after the sitting motion ends, a memory that stores the measurement data, and a processor that controls the support mechanism. The processor detects the sitting motion and identifies the chair type based on the first measurement data, detects the start of a motion of the user standing from the chair based on the second measurement data, and outputs assist information corresponding to the identified chair type and used by the support mechanism to assist the user with standing.

19 Claims, 23 Drawing Sheets

(51) Int. Cl.
*A61B 5/00* (2006.01)
*A61B 5/11* (2006.01)
*A61H 3/02* (2006.01)
*A61H 3/00* (2006.01)
*A61H 1/02* (2006.01)
*B25J 9/00* (2006.01)
*A61B 5/0488* (2006.01)

(52) U.S. Cl.
CPC .............. *A61H 1/02* (2013.01); *A61H 1/0237* (2013.01); *A61H 3/00* (2013.01); *A61H 3/02* (2013.01); *B25J 9/0006* (2013.01); *A61B 5/0488* (2013.01); *A61B 5/6828* (2013.01); *A61G 5/14* (2013.01); *A61H 2201/165* (2013.01); *A61H 2201/1642* (2013.01); *A61H 2201/5007* (2013.01); *A61H 2201/5035* (2013.01); *A61H 2201/5041* (2013.01); *A61H 2201/5064* (2013.01); *A61H 2201/5069* (2013.01); *A61H 2201/5079* (2013.01); *A61H 2201/5084* (2013.01)

(58) Field of Classification Search
CPC .......... A61H 1/0237; A61H 3/00; A61H 3/02; A61H 2201/1642; A61H 2201/165; A61H 2201/5007; A61H 2201/5035; A61H 2201/5041; A61H 2201/5064; A61H 2201/5079; A61H 2201/5084; B25J 9/0006; A61G 5/14
USPC .......................................................... 601/35
See application file for complete search history.

FIG. 7

| MEASUREMENT DATE AND TIME | TIBIALIS ANTERIOR MUSCLE | GASTROCNEMIUS MUSCLE | VASTUS MEDIALIS MUSCLE | ... | ACCELERATION x | ACCELERATION y | ACCELERATION z | ANGULAR VELOCITY x | ... |
|---|---|---|---|---|---|---|---|---|---|
| 2014/02/05 19:00:10.005 | -1.811 | 11.029 | -33.485 | 1.584 | 1.015 | 0.029 | -0.267 | ... | ... |
| 2014/02/05 19:00:10.006 | -9.284 | 2.282 | -27.705 | 3.153 | 1.011 | 0.027 | -0.265 | ... | ... |
| 2014/02/05 19:00:10.007 | -4.145 | 0.307 | -15.968 | -17.017 | 1.007 | 0.033 | -0.269 | ... | ... |
| 2014/02/05 19:00:10.008 | 14.319 | 6.866 | 0.161 | 2.697 | 1.006 | 0.039 | -0.266 | ... | ... |
| 2014/02/05 19:00:10.009 | 34.121 | 15.559 | 15.501 | 22.389 | 1.007 | 0.047 | -0.275 | ... | ... |
| 2014/02/05 19:00:10.010 | 39.039 | 16.868 | 23.266 | 31.848 | 1.013 | 0.052 | -0.279 | ... | ... |
| 2014/02/05 19:00:10.011 | 23.202 | 7.105 | 19.96 | 24.433 | 1.017 | 0.056 | -0.278 | ... | ... |
| 2014/02/05 19:00:10.012 | -2.73 | -7.7 | 8.673 | 5.714 | 1.012 | 0.062 | -0.274 | ... | ... |
| 2014/02/05 19:00:10.013 | -20.884 | -17.114 | -3.016 | -11.596 | 1.013 | 0.064 | -0.272 | ... | ... |
| 2014/02/05 19:00:10.014 | -20.803 | -15.542 | -8.358 | -17.289 | 1.014 | 0.067 | -0.277 | ... | ... |
| 2014/02/05 19:00:10.015 | -8.539 | -6.405 | -6.033 | -11.181 | 1.01 | 0.076 | -0.279 | ... | ... |
| 2014/02/05 19:00:10.016 | 2.391 | 1.564 | -0.341 | -1.969 | 1.001 | 0.075 | -0.274 | ... | ... |
| 2014/02/05 19:00:10.017 | 3.198 | 3.153 | 2.773 | 1.152 | 1 | 0.077 | -0.279 | ... | ... |
| ... | ... | ... | ... | ... | ... | ... | ... | ... | ... |

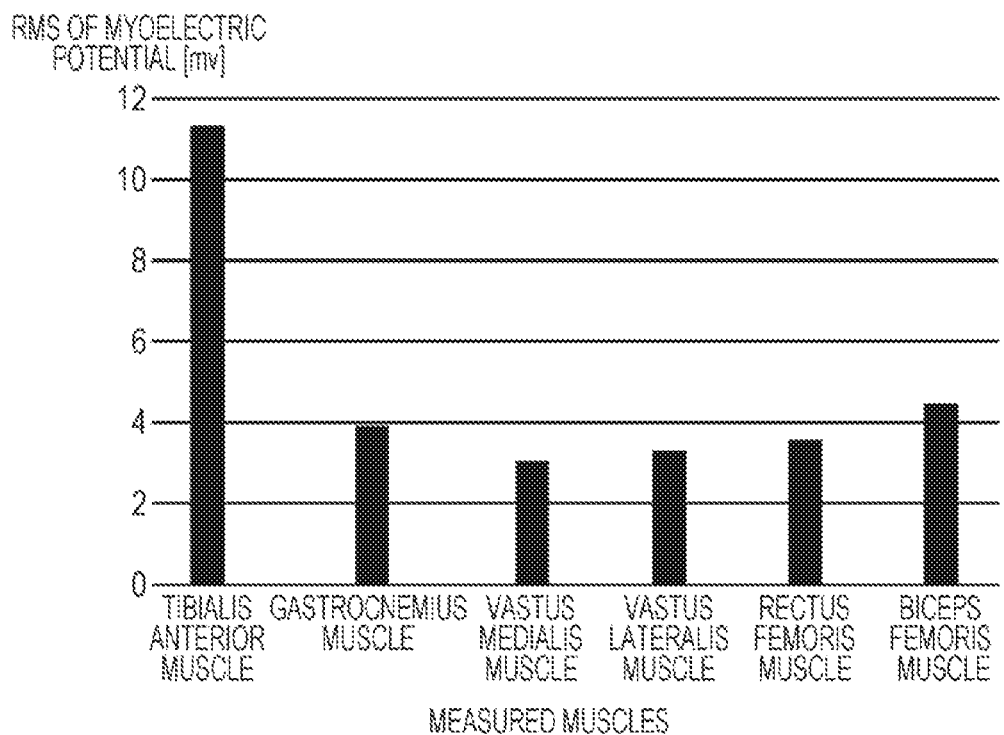

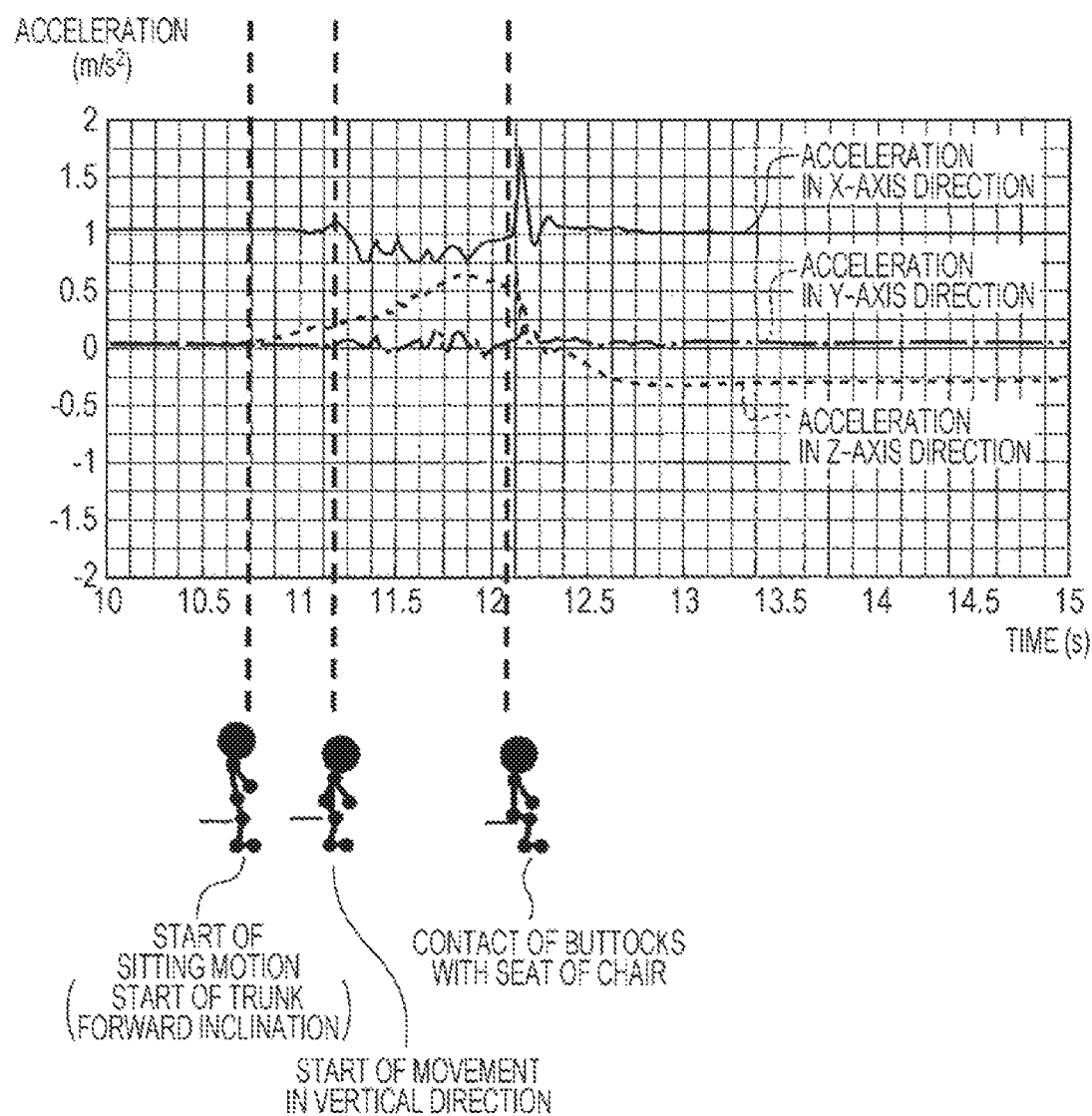

| PARAMETER | THRESHOLD VALUE |
|---|---|
| ACCELERATION IN X-AXIS DIRECTION | 0.9 m/s² |
| ACCELERATION IN Z-AXIS DIRECTION | 0.1 m/s² |
| TRUNK FORWARD INCLINATION ANGLE | 70 deg |

FIG. 15

| TYPE OF CHAIR | | THRESHOLD VALUE OF TRUNK FORWARD INCLINATION ANGLE |
|---|---|---|
| TYPE 1 | | 110 deg |
| TYPE 2 | | 120 deg |
| TYPE 3 | | 130 deg |

FIG. 22
| TYPE OF CHAIR | THRESHOLD VALUE OF MYOELECTRIC POTENTIAL |
|---|---|
| TYPE 4 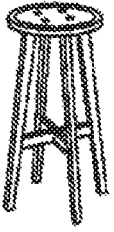 | THRESHOLD VALUE: Th4 |
| TYPE 2  | THRESHOLD VALUE: Th2 |
| TYPE 3 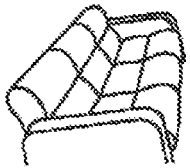 | THRESHOLD VALUE: Th3 |
Th4 < Th2 < Th3

STANDING MOTION ASSIST DEVICE, STANDING MOTION ASSIST METHOD, AND RECORDING MEDIUM

BACKGROUND

1. Technical Field

The present disclosure relates to a standing motion assist device, a standing motion assist method, and a recording medium that support a user with a standing motion.

2. Description of the Related Art

In recent years, standing motion assist devices (also referred to as a leg support orthosis or a power assist suit) that supports a user, such as an elderly person, with a standing motion have been developed (refer to, for example, Japanese Unexamined Patent Application Publication No. 2010-253048).

SUMMARY

However, a situation arises in which the standing motion assist device described in Japanese Unexamined Patent Application Publication No. 2010-253048 cannot appropriately support a user with a standing motion.

Accordingly, one non-limiting and exemplary embodiment provides a standing motion assist device, a standing motion assist method, and a recording medium capable of appropriately supporting a user with a standing motion.

In one general aspect, the techniques disclosed here feature a standing motion assist device. A standing motion assist device includes a support mechanism attached to a leg of a user to assist the user with motion, a sensor including at least one of a first sensor and a second sensor, the first sensor measuring posture information in accordance with postures of the user and outputting the posture information, the second sensor measuring myoelectric potential information including myoelectric potentials of the user and outputting the myoelectric potential information, the sensor outputting measurement data including at least one of the posture information and the myoelectric potential information, a memory that stores the measurement data, and a processor that controls the support mechanism by using the measurement data stored in the memory. The processor detects a sitting motion of the user sitting in a chair on the basis of the measurement data. The detection of the sitting motion includes a detection of a start of the sitting motion and a detection of an end of the sitting motion. The processor identifies a type of the chair on the basis of first measurement data included in the measurement data and measured after the start of the sitting motion. The processor detects a start of a standing motion of the user standing from the chair on the basis of second measurement data included in the measurement data and measured after the end of the sitting motion. The processor outputs assist information used to cause the support mechanism to assist the user with the standing motion in accordance with the identified type of the chair.

The standing motion support device of the present disclosure is capable of appropriately supporting a user with a standing motion.

It should be noted that general or specific embodiments may be implemented as a system, a method, an integrated circuit, a computer program, a computer-readable storage medium or any selective combination thereof. Examples of a storage medium include a nonvolatile storage medium, such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 illustrates an example of measurement data stored in a measurement data storage unit according to the exemplary embodiment;

FIG. 8A illustrates an example of RMS of the myoelectric potential calculated for each of the muscles of a user sitting on a wooden chair according to the exemplary embodiment;

FIG. 8B illustrates an example of the sitting conditions stored in the sitting condition storage unit according to the exemplary embodiment;

FIG. 9 illustrates an example of the acceleration measured when a user is sitting down on a wooden chair;

FIG. 15 illustrates another example of the chair condition for the sitting duration stored in the chair condition storage unit according to the exemplary embodiment;

FIG. 22 illustrates an example of the standing condition stored in a standing condition storage unit according to the modification of the exemplary embodiment.

DETAILED DESCRIPTION

Figure 1A:
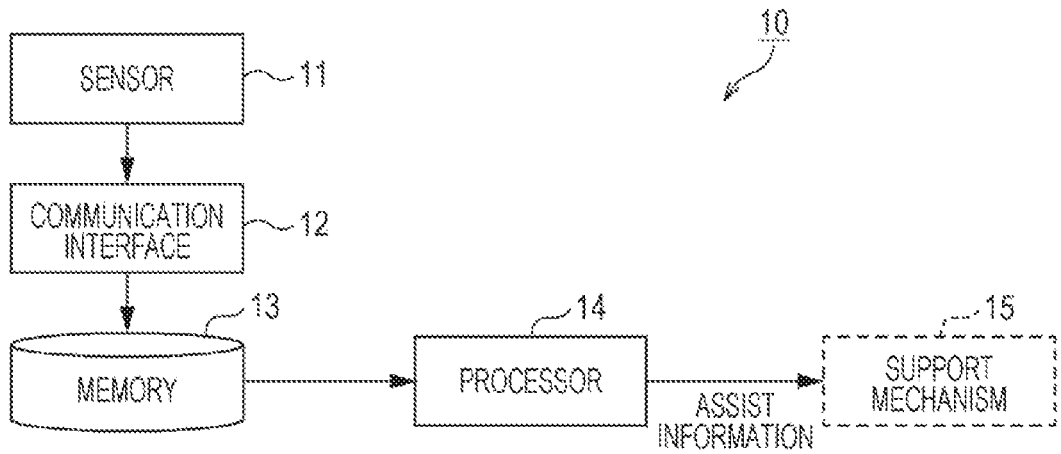
FIG. 1A is a schematic functional block diagram of a standing motion assist device according to an exemplary embodiment.

The present inventor found that the following situation arises in the standing motion assist device of Japanese Unexamined Patent Application Publication No. 2010-253048 described in "Background Art".

Upon detecting a standing motion of a user which starts from a sitting posture in a chair, existing wearable standing motion assist devices as described in Japanese Unexamined Patent Application Publication No. 2010-253048 assists the user with a standing motion by using a constant force and a constant speed regardless of the type of chair in which the user is sitting.

However, in the daily life, it is common for a user to sit in a plurality of different types of chairs. In these multiple types of chairs, the height of the seat s different, and the position of the feet of the user during the standing motion is different. Thus, for example, when the user sits in a chair having a low seat, such as a sofa, and attempts to stand up, their buttocks are lowered and their knees are straight, such that the user is unable to deeply bend their knees. At this time, a relatively strong force is needed to assist the user with a standing motion. In contrast, when the user sits in a chair having a higher seat than a sofa, such as an office chair, the user can be seated with their buttocks at a high position and, thus, relatively freely bend their knees. Thus, the user stands up while bending their knees deeply. At this time, a relatively weak force is sufficient to assist the user with a standing motion.

However, as described above, existing standing motion assist devices assist the users by using a constant force and speed regardless of the type of chair in which the user is sitting. Accordingly, the power may be insufficient to assist a user sitting in a sofa with a standing motion, or an excessive force may be applied to assist a user sitting in an office chair with a standing motion. As a result, the standing motion of the user becomes unstable.

According to an aspect of the present disclosure, a standing motion assist device includes a support mechanism attached to a leg of a user to assist the user with motion, a sensor including at least one of a first sensor and a second sensor, the first sensor measuring posture information in accordance with postures of the user and outputting the posture information, the second sensor measuring myoelectric potential information including myoelectric potentials of the user and outputting the myoelectric potential information, the sensor outputting measurement data including at least one of the posture information and the myoelectric potential information, a memory that stores the measurement data, and a processor that controls the support mechanism by using the measurement data stored in the memory. The processor detects a sitting motion of the user sitting in a chair on the basis of the measurement data. The detection of the sitting motion includes a detection of a start of the sitting motion and a detection of an end of the sitting motion. The processor identifies a type of the chair on the basis of first measurement data included in the measurement data and measured after the start of the sitting motion. The processor detects a start of a standing motion of the user standing from the chair on the basis of second measurement data included in the measurement data and measured after the end of the sitting motion. The processor outputs assist information used to cause the support mechanism to assist the user with the standing motion in accordance with the identified type of the chair. For example, the myoelectric potential information may include first myoelectric potentials of a muscle included in muscles in a leg of the user. In addition, the posture information may be at least one of accelerations, angular velocities, and geomagnetisms of an upper body of the user.

In this manner, the type of the chair is identified on the basis of biometric values of a user acquired after the user starts a sitting motion, and the support mechanism assists the user with standing motion in accordance with the type of the chair. Consequently, an insufficient or excessive force to assist the user with the standing motion can be prevented, which makes the standing motion of the user stable. As a result, the standing motion assist device can assist the user with a standing motion in an appropriate manner. In other words, since the standing motion assist device according to one embodiment of the present disclosure can assist the user with a standing motion by using a force or a speed corresponding to the type of the chair in which the user is sitting, a stable standing motion can be provided to the user. Furthermore, since an excessive force is prevented from being applied, extra energy is not consumed and, thus, the battery-powered standing motion assist device can be used for a longer period of time.

In addition, the measurement data may include the first myoelectric potentials. If a myoelectric potential, included in the first myoelectric potentials, is greater than or equal to a threshold value corresponding to the muscle, the processor may detect the start of the sitting motion.

During the sitting motion, a large myoelectric potential is generated in a predetermined muscle, such as the tibialis anterior muscle. Accordingly, by detecting the start of the sitting motion on the basis of the myoelectric potential as described above, the sitting motion can be detected at an appropriate point in time.

In addition, the measurement data may include the accelerations. The processor may calculate movement distances by which the upper body of the user moves in a vertical direction on the basis of the accelerations. If a movement distance, included in the movement distances, is greater than or equal to a threshold value, the processor may detect the sitting motion.

During the sitting motion, the upper body moves largely in the vertical direction. Accordingly, by detecting the sitting motion on the basis of the movement distance of the upper body as described above, the sitting motion can be detected at an appropriate point in time.

In addition, the measurement data may include the accelerations. The measurement data may include third measurement data and fourth measurement data measured later than the third measurement data. The third measurement data may include first accelerations, and the fourth measurement data may include second accelerations. The accelerations may include the first accelerations and the second accelerations. If the magnitude of the vertically downward component of an acceleration, included in the first accelerations, is greater than or equal to a first threshold value and a magnitude of a vertically upward component of an acceleration, included in the second acceleration, is greater than or equal to a second threshold value, the processor may detect the sitting motion.

When buttocks of the user who is sitting down are brought into contact with the seat of the chair, a large upward acceleration in the vertically upward direction occurs. Accordingly, by detecting the sitting motion on the basis of the vertical upward acceleration as described above, the sitting motion can be detected at an appropriate point in time.

In addition, the posture information may be angular velocities of the upper body of the user. The measurement data may include the angular velocities. The processor may calculate trunk forward inclination angles of the user on the basis of the angular velocities. If myoelectric potentials, included in the myoelectric potentials, increases as time passes within a predetermined time period after a trunk forward inclination angle, included in the trunk forward inclination angles reaches a value less than a threshold value, the processor may detect the start of the sitting motion.

In this manner, since the sitting motion is detected on the basis of the trunk forward inclination angle and the myoelectric potential, the start of the sitting motion can be detected at a more appropriate point in time.

In addition, the processor may identify the type of the chair by using at least one of (i) data included in the measurement data and measured for a first duration during which the sitting motion is being performed and (ii) data included in the measurement data and measured for a second duration during which the user remains sitting.

In this manner, the type of the chair is identified in accordance with at least one of the measurement result for the first duration during which the sitting motion is being performed and the measurement result for the second duration during which the user remains sitting. Accordingly, when, for example, the type of the chair is identified in accordance with the measurement results for the first duration and the second duration, the reliability of identifying the type of the chair can be increased.

In addition, the myoelectric potentials may be myoelectric potentials of a muscle in a leg of the user. The measurement data may include the myoelectric potentials of the muscle in the leg of the user. The processor may identify the type of the chair by determining whether the myoelectric potentials meet a condition which is defined for each of a plurality of types of chairs.

Even when the sitting motion is performed and when the user remains sitting, different myoelectric potentials are generated in accordance with the type of the chair. Accordingly, by identifying the type of the chair on the basis of the myoelectric potentials as described above, the reliability of identifying the type of the chair can be increased more.

In addition, the posture information may be accelerations of an upper body of the user. The measurement data may include the accelerations. After the sitting motion starts, the processor may calculate a movement distance by which the upper body of the user moves in a vertical direction on the basis of magnitudes of vertically upward components of the accelerations and identify the type of the chair in accordance with the movement distance.

The vertical movement distance of the upper body of the user who is sitting down differs according to the height of the seat of the chair. Accordingly, by identifying the type of the chair on the basis of the movement distance as described above, the reliability of identifying the type of the chair can be increased more.

In addition, the posture information may be accelerations of an upper body of the user. The measurement data may include the accelerations. The processor may calculate a maximum rate of change of accelerations in a vertical direction based on accelerations, included in the accelerations, during a predetermined time period from the start of the sitting motion and identify the type of the chair in accordance with the maximum rate of change.

The maximum rate of change of acceleration in the vertical upward direction which occurs when buttocks of the user are brought into contact with the seat of the chair differs according to the hardness of the seat of the chair. Accordingly, by identifying the type of the chair on the basis of the maximum rate of change of the acceleration as described above, the reliability of identifying the type of the chair can be increased more.

In addition, the posture information may be an angular velocity of an upper body of the user. The measurement data may include angular velocities. The processor may calculate trunk forward inclination angles of the user by using first angular velocities, included in the angular velocities, for a duration during which the user remains sitting after the sitting motion ends and identify the type of the chair in accordance with the trunk forward inclination angles.

The maximum value of the trunk forward inclination angle of the user who remains sitting differs according to the angle of a backrest of the chair. Accordingly, as described above, by identifying the type of the chair on the basis of the trunk forward inclination angles, the reliability of identifying the type of the chair can be increased more.

In addition, the second sensor may include two or more myoelectric potential measurement sensors, the two or more myoelectric potential measurement sensors measuring the myoelectric potentials of muscles in the leg of the user. The measurement data may include the myoelectric potentials. The processor may identify an order in which the muscles start their activities thereof on the basis of the myoelectric potentials and detect the start of the sitting motion if the identified order is the same as a predetermined order.

When a user who is sitting stands up, muscles of the legs of the users start their activities in a predetermined order. Accordingly, as described above, by detecting the start of the standing motion on the basis of the order in which the muscles start their activities, the start of the standing motion can be detected at an appropriate point in time.

In addition, the posture information may be angular velocities of the upper body of the user. The measurement data may include the angular velocities of the upper body of the user. The processor may calculate trunk forward inclination angles of the user based on the angular velocities and identify the order after a trunk forward inclination angle, included in the trunk forward inclination angles, reaches a threshold value or less.

When the user who is sitting stands up, muscles of the legs of the user start their activities in a predetermined order after the trunk forward leaning motion is performed. Accordingly, as described above, by detecting the start of the standing motion on the basis of the order after the trunk forward inclination angle reaches the threshold value or less, the standing motion can be detected at a more appropriate point in time.

In addition, the processor may change the threshold value in accordance with the identified type of the chair.

Thus, since the start of the standing motion is detected on the basis of the type of the chair in which the user is sitting, the start of the standing motion can be detected highly accurately.

In addition, the myoelectric potentials may be myoelectric potentials of muscles in a leg of the user. The measurement data may include the myoelectric potentials. The processor may acquire an identification threshold value. The identification threshold value may decrease with increasing height of a seat of the chair. The processor may detect the start of the standing motion if a myoelectric potential, included in the myoelectric potentials and measured after the sitting motion, reaches the identification threshold value or greater.

In this manner, the start of the standing motion can be detected at an appropriate point in time in accordance with the type of the chair in which the user is sitting.

The processor may output the assist information used to cause the support mechanism to change an angle of a knee joint of the user by using a force or a speed in accordance with the identified type of the chair.

In this manner, the standing motion assist device can support the user with a standing motion so as to extend the knee joint of the user by using a force or a speed corresponding to the type of the chair.

Exemplary embodiments are described in detail below with reference to the accompanying drawings.

Note that each of the embodiments described below is a general or specific example of the present disclosure. A value, a shape, a material, a constituent element, the positions and the connection form of the constituent elements, steps, and the sequence of steps described in the embodiments are only examples and shall not be construed as limiting the scope of the present disclosure. In addition, among the constituent elements in the embodiments described below, the constituent element that does not appear in an independent claim, which has the broadest scope, is described as an optional constituent element.

In addition, all of the drawings are schematic and not necessarily to scale. Throughout the drawings, the same reference numerals are used to designate the same constituent elements.

EXEMPLARY EMBODIMENT

Overview

FIG. 1A is a schematic functional block diagram of a standing motion assist device according to the present exemplary embodiment. As illustrated in FIG. 1, a standing motion assist device 10 includes a sensor 11, a communication interface 12, a memory 13, a processor 14, and a support mechanism 15.

The support mechanism 15 is attached to the legs of a user and supports the user with motion. The sensor 11 continuously measures at least one of a numerical value and a myoelectric potential corresponding to the posture of the user, which is a biological value of the user, and outputs measurement data indicating the continuously measured biological values of the user. The communication interface 12 acquires the measurement data output from the sensor 11 and stores the measurement data in the memory 13. The processor 14 controls the support mechanism 15 by using the measurement data stored in the memory 13.

More specifically, the processor 14 detects the start to the end of the sitting motion of the user sitting down on the chair on the basis of the measurement data. Upon detecting a sitting motion, the processor 14 identifies the type of chair on the basis of the biological value of the user indicated by the measurement data acquired after the start of the sitting motion. Subsequently, the processor 14 detects the start of a standing motion of the user standing up from the chair on the basis of the biological value of the user indicated by the measurement data acquired after the sitting motion. Subsequently, the processor 14 outputs assist information used to cause the support mechanism 15 to assist the user with the standing motion in accordance with the identified type of chair. While the standing motion assist device 10 according to the present exemplary embodiment includes the support mechanism 15, the support mechanism 15 does not necessarily have to be included in the standing motion assist device 10.

Figure 1B:
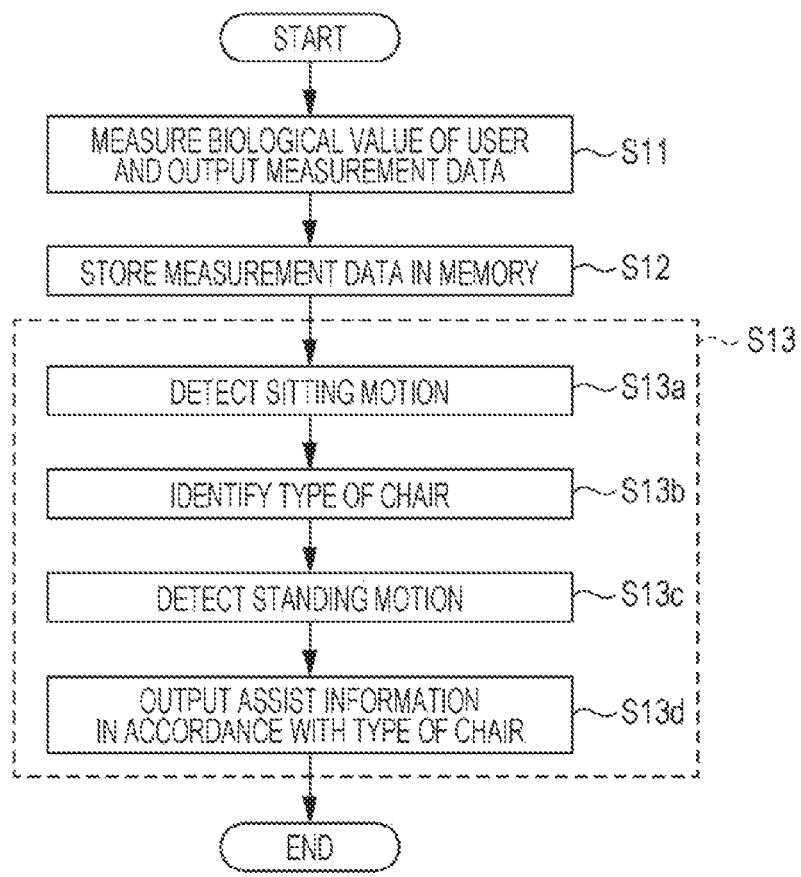
FIG. 1B is a schematic flowchart of a standing motion assist method according to an exemplary embodiment.

FIG. 1B is a schematic flowchart of a standing motion assist method according to the present exemplary embodiment. In the standing motion assist method, the sensor 11 continuously detects at least one of a numerical value and a myoelectric potential corresponding to the posture of a user as a biological value of the user first. Thereafter, the sensor 11 outputs the continuously measured biological values of the user (step S11).

Subsequently, the communication interface 12 acquires the measurement data output from the sensor 11 and stores the acquired data in the memory 13 (step S12).

Subsequently, the processor 14 controls the support mechanism 15 attached to the legs of the user by using the measurement data stored in the memory 13 (step S13).

More specifically, in step S13, the processor 14 detects the start to the end of the sitting motion of the user sitting in a chair on the basis of the measurement data (step S13a). Subsequently, upon detecting the sitting motion, the processor 14 identifies the type of chair on the basis of the biometric value of the user indicated by the measurement data acquired after the start of the sitting motion (step S13b). Subsequently, the processor 14 detects the start of a standing motion of the user from the chair on the basis of the biological value of the user indicated by the measurement data acquired after the sitting motion (step S13c). Subsequently, the processor 14 outputs assist information used by the support mechanism 15 to support the user with a standing motion in accordance with the identified type of chair (step S13d).

In this manner, the type of chair is identified on the basis of the biometric value of the user acquired after the start of the sitting motion, and the support mechanism 15 supports the user with the standing motion in accordance with the type of chair. Thus, an insufficient force or an excess force can be prevented from being applied when supporting with the standing motion in accordance with the type of chair. As a result, the user can perform the standing motion stably regardless of the type of chair.

Figure 2:
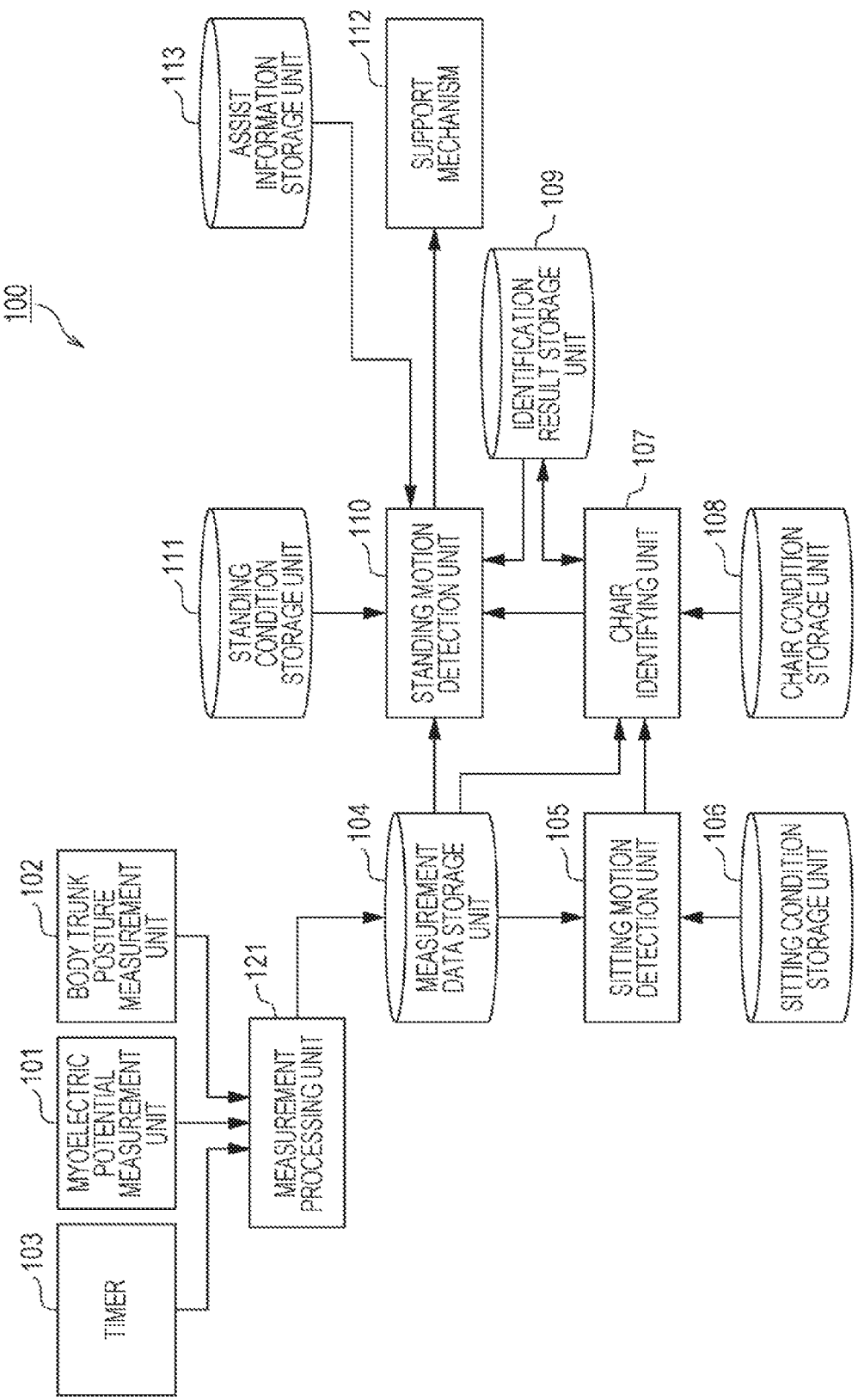
FIG. 2 is a detailed functional block diagram of the standing motion assist device according to the present exemplary embodiment.

The standing motion assist device and the standing motion assist method are described in more detail below.
Device Configuration FIG. 2 is a detailed functional block diagram of the standing motion assist device according to the present exemplary embodiment. As illustrated in FIG. 2, a standing motion assist device 100 includes a myoelectric potential measurement unit 101, a body trunk posture measurement unit 102, a timer 103, a measurement data storage unit 104, a sitting motion detection unit 105, a sitting condition storage unit 106, a chair identifying unit 107, a chair condition storage unit 108, an identification result storage unit 109, a standing motion detection unit 110, a standing condition storage unit 111, a support mechanism 112, an assist information storage unit 113, and a measurement processing unit 121. Note that the standing motion assist device 100 illustrated in FIG. 2 is a particular form of the standing motion assist device 10 illustrated in FIG. 1. In addition, the myoelectric potential measurement unit 101 and the body trunk posture measurement unit 102 illustrated in FIG. 2 correspond to the sensor 11 illustrated in FIG. 1. The measurement processing unit 121, the measurement data storage unit 104, and the support mechanism 112 illustrated in FIG. 2 correspond to the communication interface 12, the memory 13, and the support mechanism 15 illustrated in FIG. 1, respectively. In addition, the sitting motion detection unit 105, the chair identifying unit 107, and the standing motion detection unit 110 illustrated in FIG. 2 correspond to the processor 14 illustrated in FIG. 1.

Figure 3:
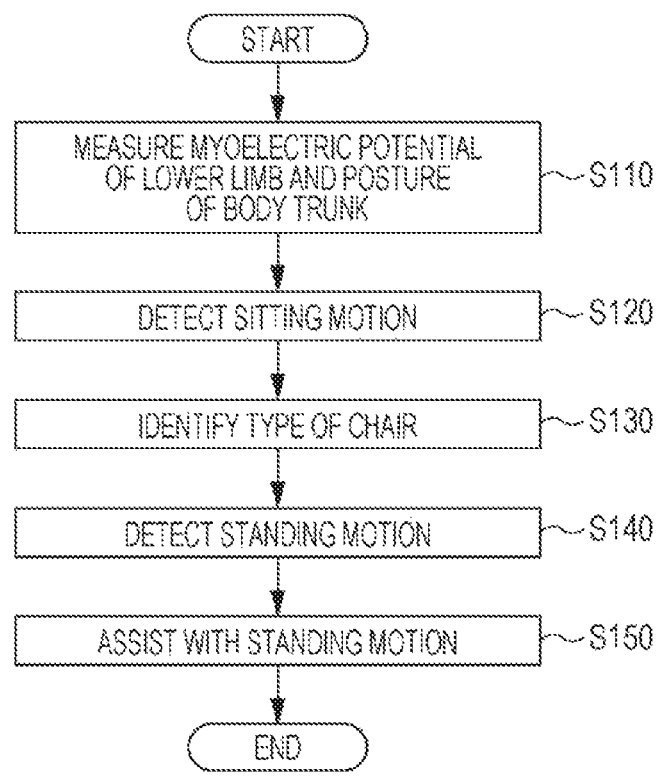
FIG. 3 is a flowchart of the overall processing performed by the standing motion assist device according to the exemplary embodiment.

FIG. 3 is a flowchart of the overall processing performed by the standing motion assist device 100.

The myoelectric potential measurement unit 101 and the body trunk posture measurement unit 102 of the standing motion assist device 100 continuously measure the myoelectric potential of the lower limb and the posture of the trunk of the user, respectively, first (step S110). The measurement processing unit 121 stores, in the measurement data storage unit 104, the measurement data acquired by the continuous measurement. Subsequently, the sitting motion detection unit 105 detects the sitting motion of the user on the basis of the measurement data stored in the measurement data storage unit 104 while referencing the sitting condition stored in the sitting condition storage unit 106 (step S120). Subsequently, by referencing the chair condition stored in the chair condition storage unit 108, the chair identifying unit 107 identifies the type of chair in which the user is sitting on the basis of the measurement data stored in the measurement data storage unit 104 (step S130). At this time, the chair identifying unit 107 stores, in the identification result storage unit 109, the identified type of chair as the identification result. Subsequently, the standing motion detection unit 110 detects the start of a standing motion of the user on the basis of the measurement data stored in the measurement data storage unit 104 while referencing the standing condition stored in the standing condition storage unit 111 (step S140). Thereafter, the support mechanism 112 acquires, from the assist information storage unit 113, assist information corresponding to the type of chair stored in the identification result storage unit 109 as the identification result. Thus, the support mechanism 112 supports the user with a standing motion in accordance with the assist information (step S150).

Timer

The timer 103 measures the current time and outputs a time signal indicating the measured time to the measurement processing unit 121. For example, the timer 103 outputs a time signal indicating the current time at intervals of 1 μs or 1 ms.

Storage Unit

The measurement data storage unit 104 is a memory or a hard disk having a storage area for storing the above-described measurement data. The sitting condition storage unit 106 is a memory or a hard disk having a storage area for storing the above-described sitting condition referenced to detect a sitting motion of the user. The chair condition storage unit 108 is a memory or a hard disk having a storage area for storing the above-mentioned chair condition referenced to identify the type of chair. The standing condition storage unit 111 is a memory or a hard disk having a storage area that stores the standing condition referenced to detect the standing motion of a user. The identification result storage unit 109 is a memory or a hard disk having a storage area for storing the type of chair identified by the chair identifying unit 107. The assist information storage unit 113 is a memory having a storage area for storing, for each of the types of chairs, assist information used to cause the support mechanism 112 to support the user who sits in a chair of that type with a standing motion.

Note that these storage units may be different hardware units. Alternatively, two or more of these storage units may be one hardware unit. That is, one memory may include the measurement data storage unit 104, the sitting condition storage unit 106, the standing condition storage unit 111, the chair condition storage unit 108, the identification result storage unit 109, and the assist information storage unit 113.

Support Mechanism

Figure 4:
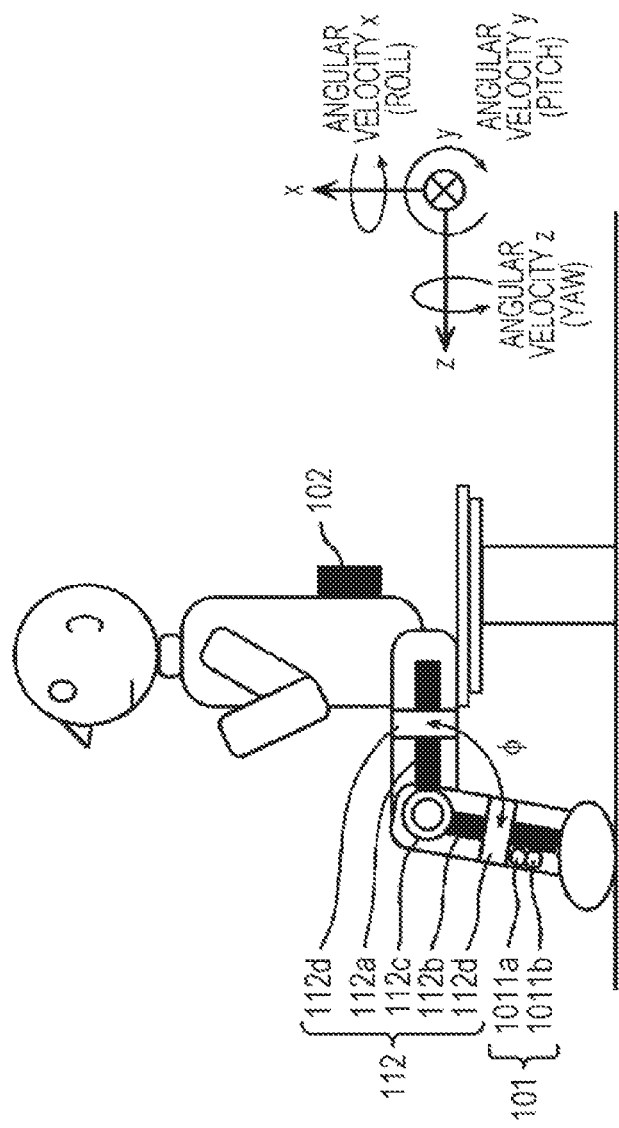
FIG. 4 is an external view of an example of the entirety or part of each of a support mechanism, a body trunk posture measurement unit, and a myoelectric potential measurement unit attached to a user according to the exemplary embodiment.

FIG. 4 is an external view of an example of the entirety or part of each of the support mechanism 112, the body trunk posture measurement unit 102, and the myoelectric potential measurement unit 101 attached to the user.

As illustrated in FIG. 4, the support mechanism 112 is attached to the legs or the lower limb of a user. The support mechanism 112 includes a thigh frame 112a, a shank frame 112b, a power unit 112c, and a fixing unit 112d. The thigh frame 112a and the shank frame 112b are disposed so as to extend along the thigh and the lower thigh of the user, respectively. The thigh frame 112a and the shank frame 112b are fixed to each of the legs of the user by the fixing unit 112d. The power unit 112c is configured to be a joint that rotatably connects the thigh frame 112a with the shank frame 112b. The power unit 112c generates power by, for example, driving a motor and increases a frame angle φ formed by the thigh frame 112a and the shank frame 112b. When the user stands up, the support mechanism 112 moves the thigh frame 112a relative to the shank frame 112b so that the power unit 112c extends the knees of the user. As a result, the legs of the user wearing the support mechanism 112 can be extended at the knees with less muscular strength so that the user can perform a standing motion with less burden.

In the example illustrated in FIG. 4, the support mechanism 112 includes one unit including the thigh frame 112a, the shank frame 112b, the power unit 112c, and the fixing unit 112d. However, two of the units may be provided in the support mechanism 112. That is, one of the two units included in the support mechanism 112 is attached to the right leg of the user, and the other unit is attached to the left leg of the user.

Body Trunk Posture Measurement Unit

As illustrated in FIG. 3, in step S110, the body trunk posture measurement unit 102 measures the posture of the body trunk of the user (that is, a numerical value corresponding to the posture). The body trunk of the user is, for example, the spine of the user. According to the present exemplary embodiment, the body trunk posture measurement unit 102 measures, as a numerical value corresponding to the posture of the body trunk, at least one of the acceleration, the angular velocity, and the geomagnetism of the upper body of the user. More specifically, the body trunk posture measurement unit 102 is configured as a nine-axis sensor including an acceleration sensor, an angular velocity sensor, and a geomagnetic sensor. As illustrated in FIG. 4, the body trunk posture measurement unit 102 is disposed on the waist of the user. The body trunk posture measurement unit 102 continuously measures the acceleration, the angular velocity, and the geomagnetism at intervals of 1 μs or 1 ms, for example. As illustrated in FIG. 4, the x-axis, the y-axis, and the z-axis are set in the body trunk posture measurement unit 102. The x-axis is, for example, an axis in the vertical direction, and a vertically upward direction is a positive direction. The y-axis is, for example, an axis that is perpendicular to the x-axis and extends in the right-left direction of the user, and the right direction is a positive direction. The z-axis is, for example, an axis perpendicular to the x-axis and extending in the front-back direction of the user, and the front direction is a positive direction. The acceleration sensor measures the acceleration of the body trunk posture measurement unit 102 in each of the x-axis direction, the y-axis direction, and the z-axis direction. The geomagnetic sensor measures the magnitude of each of the geomagnetic components in the x-axis direction, the y-axis direction, and the z-axis direction and combines the magnitudes of the geomagnetic components. In this manner, the geomagnetic sensor measures the direction and the magnitude of the geomagnetism. The angular velocity sensor measures an angular velocity x (roll) about the x-axis serving as the rotation center, an angular velocity y (pitch) about the y-axis serving as the rotation center, and an angular velocity z (yaw) about the z-axis serving as the rotation center.

In addition, the numerical value corresponding to the posture, such as the acceleration, measured by the body trunk posture measurement unit 102 may be a measured value obtained directly from the nine-axis sensor or a value corresponding to the measured value. A value corresponding to the measured value is a value obtained by performing processing, such as amplification, rectification, or filtering, on the directly measured value. That is, the numerical value corresponding to the posture may be a measured value obtained directly from the nine-axis sensor or may be a value calculated or processed by using the measured value.

Myoelectric Potential Measurement Unit

As illustrated in FIG. 3, in step S110, the myoelectric potential measurement unit 101 measures, as the myoelectric potential, the myoelectric potential of at least one muscle in the legs of the user. More specifically, the myoelectric potential measurement unit 101 continuously measures the myoelectric potential at intervals of 1 μs or 1 ms, for example. Myopotential is an electrical potential that changes in response to a movement command generated in the brain or spinal cord so as to induce muscle contraction that occurs on the muscle fiber. As a stronger muscle force is exerted, a larger value of myopotential is measured. The myoelectric potential measurement unit 101 uses two electrodes for measurement of one myoelectric potential and uses bipolar induction for measuring the difference between the potentials measured by the two electrodes. For example, as illustrated in FIG. 4, the myoelectric potential measurement unit 101 measures the surface myoelectric potential at a given portion of the lower limb of the user by using electrodes 1011a and 1011b attached to the portion.

Figure 5:
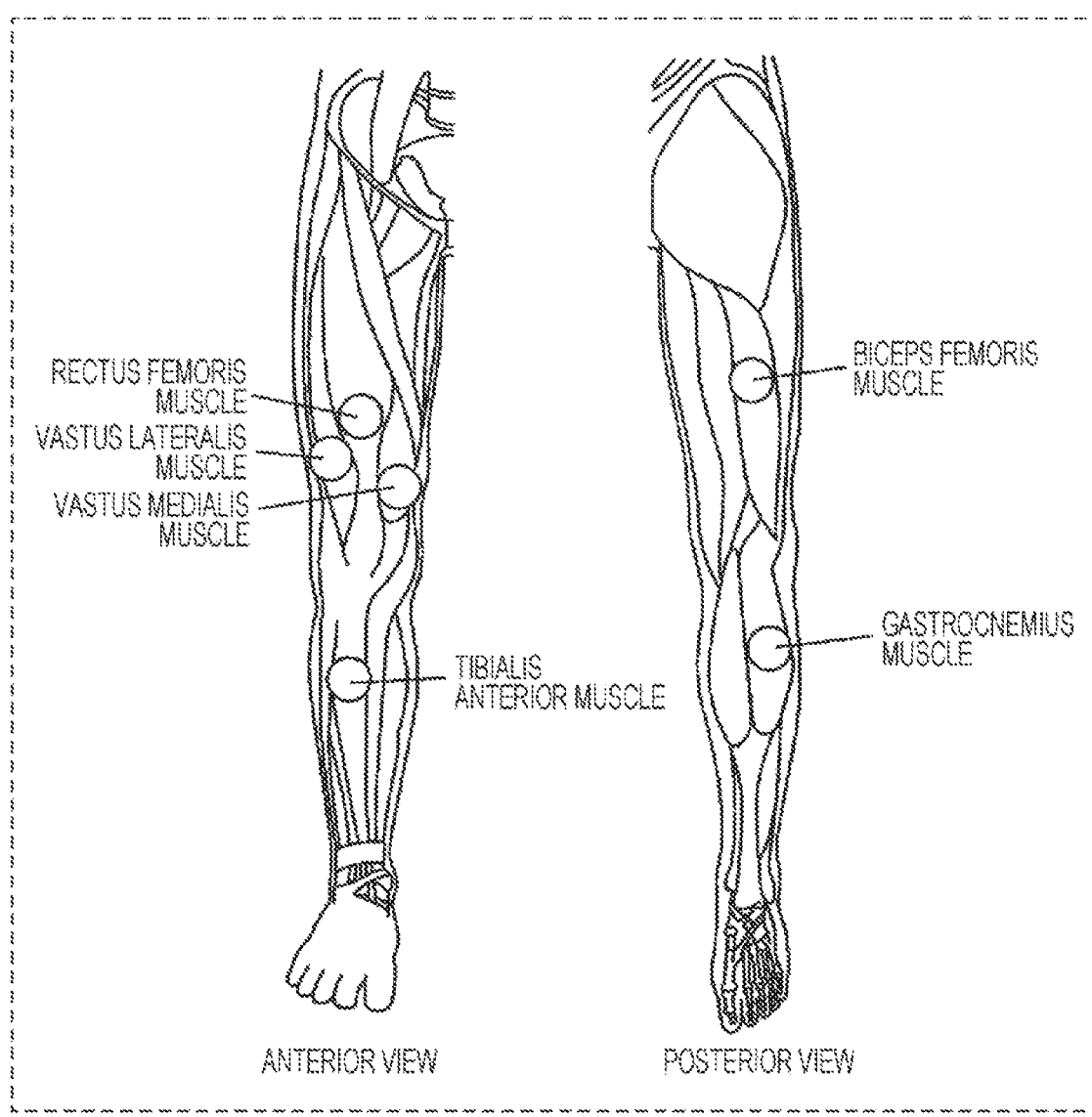
FIG. 5 illustrates an example of muscles measured by the myoelectric potential measurement unit according to the exemplary embodiment.

FIG. 5 illustrates an example of muscles measured by the myoelectric potential measurement unit 101. More specifically, the myoelectric potential measurement unit 101 measures the myoelectric potentials of the tibialis anterior muscle, the gastrocnemius muscle, the vastus medialis muscle, vastus lateralis muscle, the rectus femoris muscle, and the biceps femoris muscle illustrated in FIG. 5. Note that the biceps femoris muscle that is likely to be in contact with the seat of the chair and one of the vastus medialis muscle and vastus lateralis muscle which output myopotentials having the same tendency may be excluded from the measurement.

Figure 6:
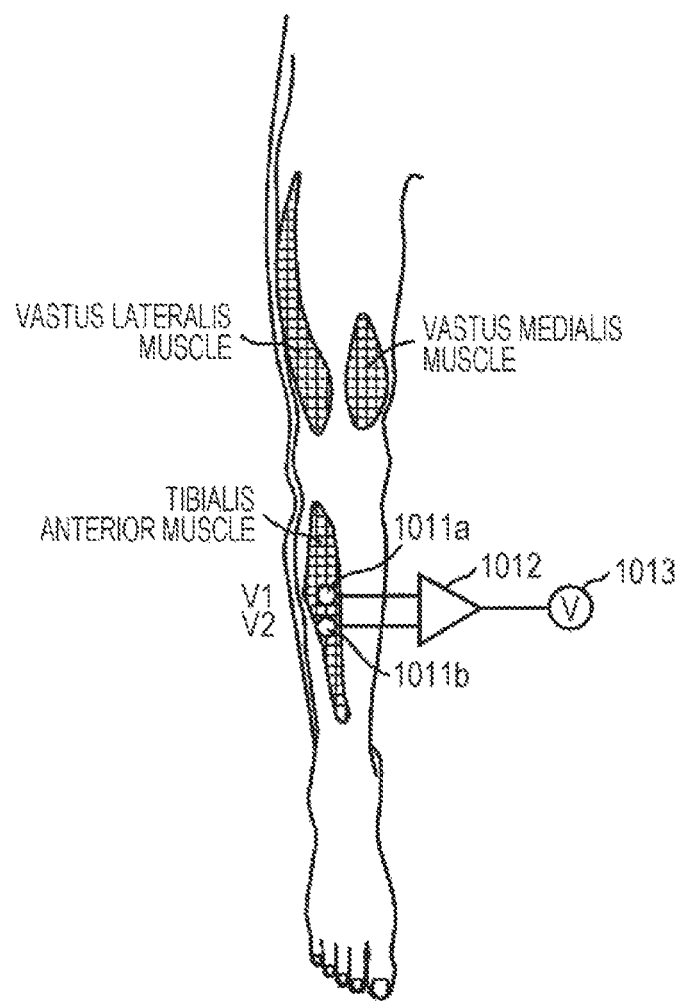
FIG. 6 illustrates an example in which the myoelectric potential measurement unit measures the myoelectric potential of a tibialis anterior muscle according to the exemplary embodiment.

FIG. 6 illustrates an example in which the myoelectric potential measurement unit 101 measures the myoelectric potential of the tibialis anterior muscle. The myoelectric potential measurement unit 101 includes the electrodes 1011a and 1011b, an amplifier 1012, and an electromyography circuit 1013.

The electrodes 1011a and 1011b are placed on the skin surface above the tibialis anterior muscle of the user. For example, the distance between the electrode 1011a and the electrode 1011b is about 10 mm to 30 mm. The amplifier 1012 amplifies the potential difference between the electrodes 1011a and 1011b, and the electromyography circuit 1013 measures the amplified potential difference as the myoelectric potential.

Note that the myoelectric potential measurement unit 101 measures the myoelectric potential of each of the above-described muscles of one leg of the user. However, the myoelectric potential measurement unit 101 may measure the myoelectric potential of each of the muscles of both legs. In this case, the myoelectric potential measurement unit 101 may output the maximum value, the minimum value, or the average value of the myoelectric potentials of the same type of muscles measured for each of the two legs. The output value is considered as the myoelectric potential of the muscle to be stored in the measurement data storage unit 104 for the type of muscle.

As described above, the myoelectric potential measured by the myoelectric potential measurement unit 101 may be a measured value obtained directly from the electrodes 1011a and 1011b or may be a value corresponding to the measured value. A value corresponding to the measured value is a value obtained by performing processing, such as amplification, full-wave rectification, or low-pass filtering, on the directly measured value. Note that full-wave rectification and low-pass filtering may be performed by the electromyography circuit 1013. That is, the myoelectric potential may be a measured value obtained directly from the electrodes or may be a value calculated or processed by using the measured value.

Measurement Processing Unit

The measurement processing unit 121 acquires the time indicated by the time signal output from the timer 103, the myoelectric potential of each of the muscles measured by the myoelectric potential measurement unit 101 at that time, and the posture of the body trunk measured by the body trunk posture measurement unit 102 at that time. Thereafter, the measurement processing unit 121 stores, in the measurement data storage unit 104, the time in association with the myoelectric potential of each of the muscles and the posture as samples of measured data.

FIG. 7 illustrates an example of measurement data stored in the measurement data storage unit 104. In an example illustrated in FIG. 7, the measurement processing unit 121 stores the samples in the measurement data storage unit 104 so that the sampling cycle is 1 KHz. The measured data indicates the sample for each of measurement dates and times 103a, which is the above-described time. That is, the measured data indicates measurement dates and times 103a each in association with myoelectric potentials 101a of the muscles and a posture 102a measured at the measurement dates and times 103a. The myoelectric potential 101a of the muscles consists of the myoelectric potentials of the tibialis anterior muscle, the gastrocnemius muscle, the vastus medialis muscle, the vastus lateralis muscle, and the biceps femoris muscle. The posture 102a consists of an acceleration x in the x-axis direction, an acceleration y in the y-axis direction, an acceleration z in the z-axis direction, an angular velocity x around the x-axis, an angular velocity y around the y-axis, an angular velocity z around the z-axis, and the direction and intensity of the geomagnetism obtained by the nine-axis sensor.

Sitting Motion Detection Unit

As illustrated in FIG. 3, in step S120, the sitting motion detection unit 105 detects the sitting motion of the user by using the measurement data stored in the measurement data storage unit 104. More specifically, the sitting motion detection unit 105 periodically acquires the myoelectric potentials of the muscles and the posture associated with the most recent measurement date and time indicated by the measurement data, for example. Subsequently, the sitting motion detection unit 105 converts the acquired myoelectric potentials or the posture into numerical values used to detect the sitting motion. Thereafter, the sitting motion detection unit 105 detects the sitting motion of the user by comparing the numerical values with the sitting condition stored in the sitting condition storage unit 106. Upon detecting the sitting motion, the sitting motion detection unit 105 transmits sitting detection information to the chair identifying unit 107. In this example, the sitting detection information indicates that the sitting motion has been detected and a sitting motion duration. The sitting motion duration is a duration from the time at which the sitting motion is started (a sitting motion start time) to a time at which the sitting motion ends (a sitting motion end time).

Method for Detecting Sitting Motion by Using Myoelectric Potential

A method for detecting a sitting motion using the myoelectric potential is described in more detail below. The sitting motion detection unit 105 periodically acquires data of a predetermined time width (for example, at intervals of 1 ms) from the measurement data stored in the measurement data storage unit 104 through the measurement in step S110 illustrated in FIG. 3. For example, the sitting motion detection unit 105 acquires data of a predetermined time width at intervals of 1 ms, and the predetermined time width is 20 ms. In this case, since the sampling frequency for the measurement data is 1 kHz, the sitting motion detection unit 105 acquires data including only 20 samples from the measurement data. Each of the samples includes the measurement date and time, the myoelectric potentials, and the posture. The sitting motion detection unit 105 calculates RMS (Root Mean Square) of the values of the myoelectric potentials of the 20 samples for each of the muscles. Thereafter, the sitting motion detection unit 105 compares the RMS with a threshold value of the myoelectric potential prestored in the sitting condition storage unit 106 as the sitting condition. If, as a result of the comparison, the RMS is greater than or equal to the threshold value, the sitting motion detection unit 105 detects the start of a sitting motion. That is, the sitting motion detection unit 105 determines that the sitting motion is started.

Note that the sitting motion detection unit 105 may detect the start of the sitting motion by using the myoelectric potential measured for a predetermined muscle at one portion or may detect the start of the sitting motion by using the myoelectric potentials measured for the muscles at a plurality of portions. For example, the sitting motion detection unit 105 may calculate the RMS of the myoelectric potentials of each of the muscles at plurality of portions. If all of the RMSs are greater than or equal to the corresponding threshold values, the sitting motion detection unit 105 may detect the start of a sitting motion. The threshold values of the muscles at the plurality of portions may differ from each other or may be the same.

As described above, if the myoelectric potentials of at least one muscle indicated by the measurement data are greater than or equal to the threshold value corresponding to the muscle, the sitting motion detection unit 105 detects the start of the sitting motion. As a result, the start of the sitting motion can be detected at a more appropriate point in time.

In addition, the sitting motion detection unit 105 may detect the start of a sitting motion on the basis of the relative relationship between the magnitudes of the myoelectric potentials measured for the muscles at a plurality of portions. More specifically, if the RMS of the myoelectric potentials measured for a predetermined one of the muscles is greater than or equal to the threshold value, the sitting motion detection unit 105 calculates the RMS of the myoelectric potentials measured for each of at least one of the muscles at the other portions. Thereafter, the sitting motion detection unit 105 may detect the start of a sitting motion by using the relative magnitude relationship among the RMSs of the muscles. For example, if the greater-lesser relationship satisfies the sitting condition stored in the sitting condition storage unit 106, the sitting motion detection unit 105 detects the start of the sitting motion.

FIG. 8A illustrates an example of the RMS of myoelectric potentials calculated for each of the muscles when the user sits down in a wooden chair. Each of the RMSs of the myoelectric potentials illustrated in FIG. 8A is the calculation result from the myoelectric potentials for 5 seconds before and after the time when the RMS of the muscle which started its activity first exceeds the threshold value. As can be seen from the calculation result in FIG. 8A, at the start of the sitting motion, the RMS of the myoelectric potential of each of the tibialis anterior muscle and the biceps femoris muscle increases, and the RMS of the myoelectric potentials of each of the vastus medialis muscle and the vastus lateralis muscle is smaller than the RMSs for the tibialis anterior muscle and the biceps femoris muscle. Accordingly, if, for example, the RMS of the myoelectric potential of the tibialis anterior muscle or the biceps femoris muscle is greater than or equal to the threshold value (for example, 4 mV or higher), the sitting motion detection unit 105 may detect the start of the sitting motion.

FIG. 8B illustrates an example of the sitting conditions stored in the sitting condition storage unit 106.

For example, as illustrated in FIG. 8B(a), the sitting condition storage unit 106 stores, as the sitting conditions, the names of muscles whose RMSs of the myoelectric potentials are to be calculated and the threshold values of the RMSs for the muscles. Note that each of the muscles whose RMS of the myoelectric potentials is to be calculated is also referred to as a "measurement channel". When the RMS of the myoelectric potentials of the tibialis anterior muscle is greater than or equal to the threshold value (for example, 5 mV) and if the RMS of the myoelectric potentials of the biceps femoris muscle is greater than or equal to the threshold value (for example 3 mV) and the RMS of the myoelectric potentials of the vastus medialis muscle is greater than or equal to the threshold value (for example 2 mV), the sitting motion detection unit 105 detects the start of the sitting motion.

Alternatively, for example, as illustrated in FIG. 8B(b), the sitting condition storage unit 106 stores, as the sitting conditions, the names of muscles whose RMS of the myoelectric potentials are to be calculated and the order of magnitude of the RMS for each of the muscles. The order of the RMS decreases with increasing RMS value. That is, this sitting condition indicates that the largest is the RMS of the myoelectric potential of the tibialis anterior muscle, followed in order by the RMSs for the biceps femoris muscle and the vastus medialis muscle. Accordingly, the sitting motion detection unit 105 detects the start of the sitting motion if the calculated RMS of the myoelectric potentials of the biceps femoris muscles is smaller than the calculated RMS of the myoelectric potentials of the tibialis anterior muscle and if the calculated RMS of the myoelectric potentials of the vastus medialis muscle is smaller than the calculated RMS of the myoelectric potentials of the biceps femoris muscle.

In addition, the sitting motion detection unit 105 determines the time at which the sitting motion is about to be detected as the sitting motion start time and determines the time immediately before the sitting motion is no longer detected as the sitting motion end time.

That is, in the case of using the myoelectric potential of a single muscle to detect a sitting motion, when the periodically calculated RMS switches from a value less than the threshold value to the threshold value or greater, the sitting motion detection unit 105 identifies a plurality of samples used for calculating the RMS (for example, 20 samples). Thereafter, the sitting motion detection unit 105 selects, from among the measurement times of the samples, the earliest time as the sitting motion start time. Subsequently, if the RMS periodically calculated after the sitting motion start time switches from the threshold value or greater to a value less than the threshold value, the sitting motion detection unit 105 identifies a plurality of samples used for calculating the RMS that is greater than or equal to the threshold value immediately before the switching (for example, 20 samples). Thereafter, the sitting motion detection unit 105 selects, from among the measurement times of the samples, the latest time as the sitting motion end time. Thus, the sitting motion duration is identified by the sitting motion start time and the sitting motion end time selected in this manner.

Furthermore, when using the myoelectric potentials of a plurality of muscles to detect the sitting motion, the sitting motion detection unit 105 may identify the sitting motion duration for each of the muscles. Thereafter, if, among the sitting motion durations identified for all of the muscles, there is at least part of duration during which all of the sitting motion durations overlap, the sitting motion detection unit 105 selects the latest (or earliest) sitting motion start time as the sitting motion start time for all of the muscles. In addition, the sitting motion detection unit 105 selects the earliest (or latest) sitting motion end time in the sitting motion durations as the sitting motion end time for all of the muscles. Note that the threshold value used to determine the sitting motion end time and the threshold value used to determine the sitting motion start time may be the same or different from each other.

Method for Detecting Sitting Motion by Using Acceleration

Subsequently, a method for detecting the sitting motion by using the acceleration measured by the nine-axis sensor is described below. The sitting motion detection unit 105 periodically acquires the most recent acceleration (for example, at intervals of 1 ms) from the measurement data stored in the measurement data storage unit 104 through the measurement in step S110 illustrated in FIG. 3.

FIG. 9 illustrates an example of the acceleration measured when the user is sitting down in the above-mentioned wooden chair. When the user is sitting down in the chair, the waist of the user moves vertically downward, so that acceleration in the vertically downward direction (the negative x-axis direction) is produced. The acceleration in the x-axis direction in FIG. 9 is about 1 m/s$^2$ because the user is subjected to gravitational acceleration even when stationary, The definition of the coordinate axes is the same as that described in "Body Trunk Posture Measurement Unit".

Thus, upon detecting that an acceleration is produced in the vertical downward direction (in the negative x-axis direction), the sitting motion detection unit 105 may detect the start of the sitting motion. However, since a change in acceleration in the vertical direction also occurs when the user squats or when the user goes up and down the stairs, a change in acceleration unique to a sitting motion may be used. More specifically, when the waist is lowered and the buttocks come into contact with the seat, a large upward acceleration is produced (that is, in the opposite direction). Thus, when the sitting motion detection unit 105 detects the occurrence of the vertical downward acceleration (that is, the acceleration in the negative x-axis direction) and, thereafter, detects an acceleration that is larger than the acceleration in the opposite direction (that is, an acceleration in the positive x-axis direction), the sitting motion detection unit 105 may determine that a sitting motion is detected. That is, in this case, the sitting motion detection unit 105 may determine that the sitting motion has started and the sitting motion has ended.

As described above, the body trunk posture measurement unit 102 measures the acceleration in the vertical direction, and the sitting motion detection unit 105 detects a sitting motion if the following conditions are met:

(a) The direction of acceleration indicated by first measurement data included in the measurement data is the vertically downward direction, and the magnitude of the acceleration is greater than or equal to a first threshold value.

(b) The direction of acceleration indicated by second measurement data measured at a time after the measurement time of the first measurement data and included in the measurement data is the vertically upward direction, and the magnitude of the acceleration is greater than or equal to a second threshold value. In this manner, the sitting motion detection unit 105 can detect the sitting motion at an appropriate point in time.

Furthermore, the sitting motion detection unit 105 may calculate the movement distance of the waist in the vertical direction by using the acceleration in the x-axis direction and detect the sitting motion on the basis of the movement distance. The height of the seat of the average chair is, for example, about 40 cm, and the lengths of the leg of the average men and women are, for example, 78.3 cm and 71.3 cm, respectively. Accordingly, by using these heights, the sitting motion detection unit 105 may determine that a sitting motion is detected if, for example, the movement distance of the body trunk posture measurement unit 102 attached to the waist of the user in the vertical direction is 30 cm or longer or between 30 cm and 40 cm. The threshold value of 30 cm or 30 to 40 cm for the movement distance may be stored in the sitting condition storage unit 106 as the sitting conditions. That is, in this case, the sitting motion detection unit 105 may determine that "the sitting motion has started and, thereafter, the sitting motion has ended", that is, the sitting motion is detected.

As described above, the body trunk posture measurement unit 102 measures the acceleration in the vertical direction, and the sitting motion detection unit 105 calculates the movement distance by which the upper body of the user moves in the vertical direction on the basis of the acceleration indicated by the measurement data. Thereafter, the body trunk posture measurement unit 102 determines that the sitting motion is detected if the movement distance is greater than or equal to the threshold value. As a result, the sitting motion can be detected at an appropriate point in time.

In addition, when a user sits down in a chair, the trunk of the user leans forward (this forward leaning motion is referred to as "trunk forward inclination motion"). At this time, as illustrated in FIG. 9, acceleration is produced in the positive z-axis direction. The trunk forward inclination motion occurs during the sitting motion, and the trunk returns to its original posture after the sitting motion. Accordingly, the sitting motion detection unit 105 may detect the start of the sitting motion when the acceleration in the positive z-axis direction and the acceleration in the x-axis direction described above occur. That is, when the acceleration in the positive z-axis direction that is greater than or equal to a threshold value is produced and the acceleration in the negative x-axis direction that is greater than or equal to a threshold value is produced, the sitting motion detection unit 105 may determine that the start of the sitting motion is detected. Furthermore, the sitting motion detection unit 105 may detect the end of the sitting motion when the acceleration in the positive x-axis direction that is greater than or equal to a threshold value is produced after the start of the sitting motion. Note that these threshold values may be stored in the sitting condition storage unit 106 as sitting conditions.

Method for Detecting Sitting Motion by Using Acceleration and Trunk Forward Inclination Angle A method for detecting a sitting motion by using the acceleration and the trunk forward inclination angle is described below. The sitting motion detection unit 105 periodically (for example, at intervals of 1 ms) acquires the most recent angular velocity around the y-axis from the measurement data stored in the measurement data storage unit 104 through the measurement in step S110 illustrated in FIG. 3. Thereafter, the sitting motion detection unit 105 calculates the trunk forward inclination angle by integrating the angular velocity over the time duration. The trunk forward inclination angle is an angle formed by the trunk of the user and the horizontal direction. The trunk forward inclination angle decreases as the user leans forward more, Note that when the user is standing, the trunk forward inclination angle is about 90 deg.

Figures 10A, 10B:
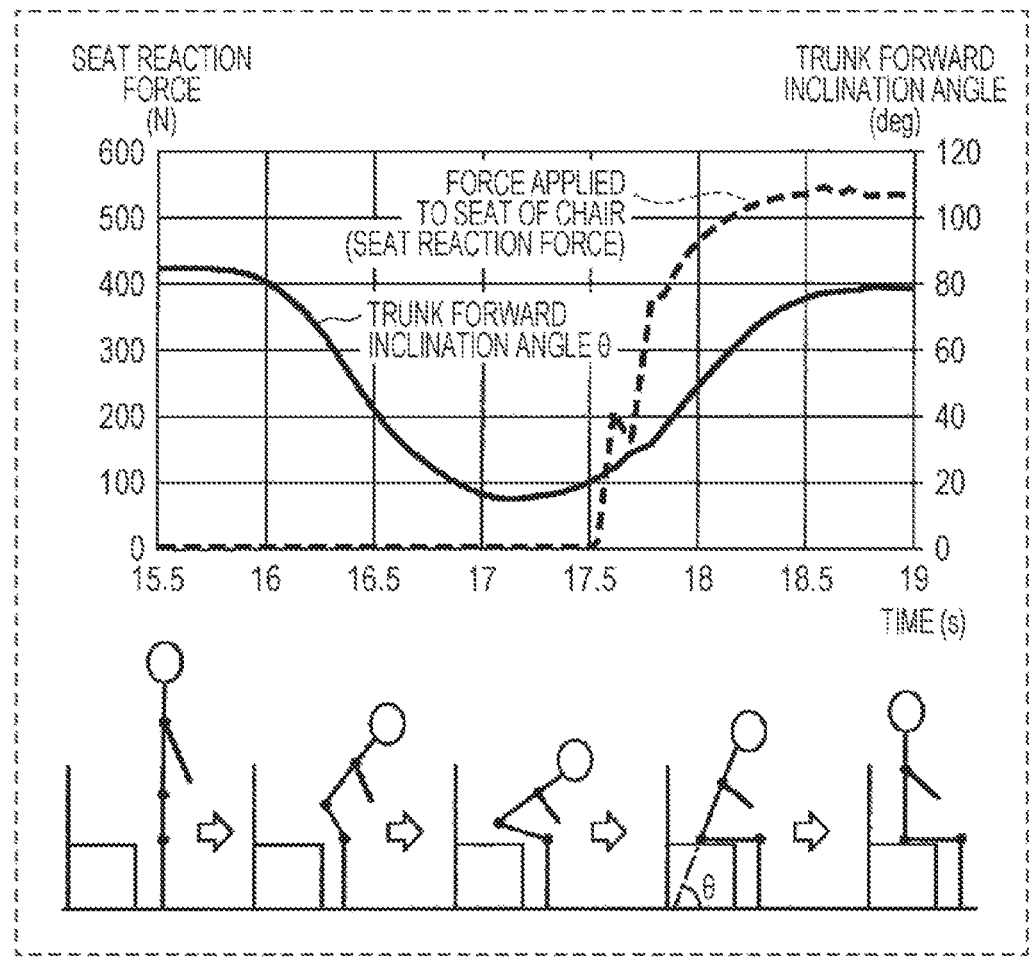
FIG. 10A illustrates an example of a trunk forward inclination angle calculated when a user is sitting down in a chair.
FIG. 10B illustrates another example of the sitting conditions stored in the sitting condition storage unit according to the exemplary embodiment.

FIG. 10A illustrates an example of a trunk forward inclination angle calculated when a user is sitting down in a chair. As illustrated in FIG. 10A, in the case where the user sits down in a chair, the force applied to the seat of the chair (known as a seat reaction force) abruptly increases when the buttocks of the user are brought into contact with the seat. In addition, the trunk forward inclination angle θ decreases immediately before the seat reaction force increases and gradually increases after the buttocks are brought into contact with the seat. Accordingly, the sitting motion detection unit 105 may detect the sitting motion, the start of the sitting motion, or the end of the sitting motion on the basis of a change in the trunk forward inclination angle θ in addition to the above-described change in acceleration.

FIG. 10B illustrates another example of the sitting conditions stored in the sitting condition storage unit 106.

For example, as illustrated in FIG. 10B, the sitting condition storage unit 106 may store, as sitting conditions, a plurality of parameters used to detect the sitting motion and the threshold values for the parameter. Examples of the parameters include the acceleration in the x-axis direction, the acceleration in the z-axis direction, and the trunk forward inclination angle. The sitting motion detection unit 105 detects the start of the sitting motion if the following conditions are met:

(a) The acceleration in the x-axis direction is less than or equal to a threshold value (for example, 0.9 m/s$^2$).
(b) The acceleration in the z-axis direction is greater than or equal to a threshold value (for example, 0.1 m/s$^2$).
(c) The trunk forward inclination angle is less than or equal to a threshold value (for example, 70 deg).

Alternatively, the sitting motion detection unit 105 may detect the sitting motion on the basis of the trunk forward inclination angle and the myoelectric potential. That is, the body trunk posture measurement unit 102 measures the myoelectric potential of at least one of the muscles in the leg of the user and, in addition, measures the angular velocity of the upper body of the user as a numerical value corresponding to the posture. Thereafter, on the basis of the angular velocity indicated by the measurement data, the sitting motion detection unit 105 continuously calculates the trunk forward inclination angle of the user. If the measured myoelectric potential increases within a predetermined period of time after the calculated trunk forward inclination angle becomes smaller than the threshold value, the sitting motion detection unit 105 detects the start of the sitting motion. In this manner, the sitting motion detection unit 105 can detect the sitting motion at a more appropriate point in time. Note that the above-described threshold value of the trunk forward inclination angle (for example, 70 deg) and the predetermined period of time may be stored in the sitting condition storage unit 106 as the sitting conditions.

Chair Identifying Unit

As illustrated in FIG. 3, in step S120, the chair identifying unit 107 receives the sitting detection information detected by the sitting motion detection unit 105. Thereafter, in step S130, the chair identifying unit 107 acquires data measured during a predetermined duration from the measurement data stored in the measurement data storage unit 104 and identifies the type of chair in which the user is sitting. The chair identifying unit 107 stores the identified type of chair in the identification result storage unit 109 as the identification result. In addition, the chair identifying unit 107 sends, to the standing motion detection unit 110, a message indicating that the identification result has been stored. The chair identifying unit 107 acquires data measured during two durations as the data measured during the predetermined duration and identifies the type of chair on the basis of the data measured during the two durations. A first one of the two durations is a sitting motion duration, and a second duration is a duration during which the user remains sitting after the sitting motion (hereinafter referred to as a "sitting duration"). The sitting motion duration, which is the first duration, may be included in the duration from the start of the sitting motion to the end of the sitting motion. The sitting duration, which is the second duration, may be included in the duration from the end of the sitting motion to the start of a standing motion.

That is, the chair identifying unit 107 identifies the type of chair by using the data measured during at least one of the first duration, which is the sitting motion duration, and the second duration, which is the sitting duration, included in the measurement data. Accordingly, for example, when the type of chair is identified on the basis of the data measured during the first duration and the second duration, the reliability of identifying the type of chair can be increased.

Method for Identifying Type of Chair by Using Myoelectric Potential

A method for identifying the type of chair by using the myoelectric potential is described first. The height, hardness, and placement restrictions of the feet differ according to the type of chair. Thus, the chair identifying unit 107 identifies the type of chair by using the characteristics that the activities of the muscles in the sitting motion duration differ according to the type of chair and the characteristic that the movement of the feet in the sitting duration differs according to the type of chair.

More specifically, the chair identifying unit 107 acquires the data in the sitting motion duration from the measurement data stored in the measurement data storage unit 104. Subsequently, the chair identifying unit 107 calculates the RMS of all the myoelectric potentials of each of the muscles in the sitting motion duration. Thereafter, the chair identifying unit 107 identifies the type of chair in which the user is sitting by comparing the chair conditions in the sitting motion duration stored in the chair condition storage unit 108 and corresponding to each of the plurality of chair types with the calculated RMS of the myoelectric potentials of each of the muscles.

As described above, when the above-described data includes the myoelectric potential, the chair identifying unit 107 identifies the type of chair by determining whether the myoelectric potentials meet the conditions of the myoelectric potentials corresponding to each of the types of chairs. In this manner, the reliability of the identified type of chair can be increased more.

Figure 11:
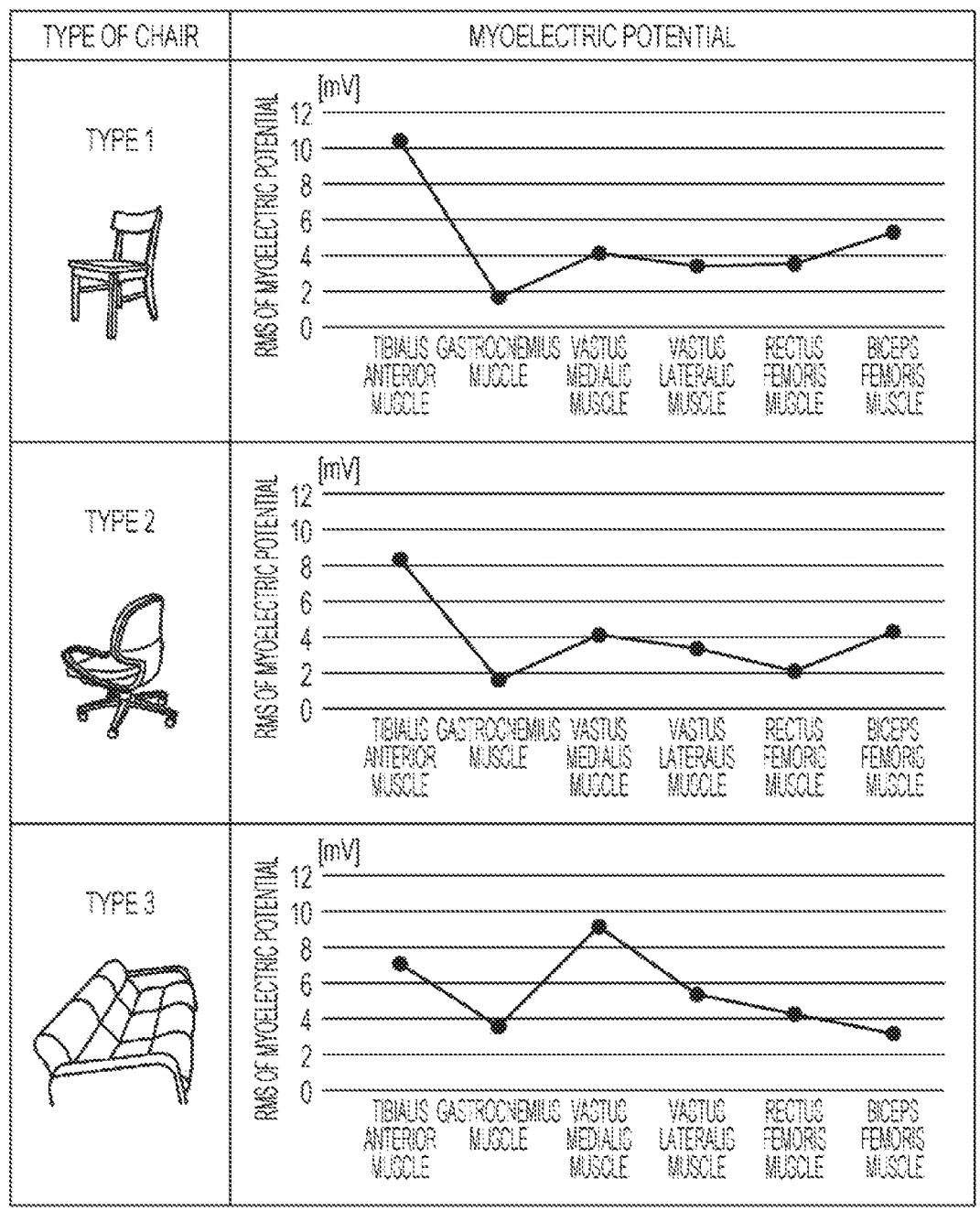
FIG. 11 illustrates an example of chair conditions for a sitting motion duration stored in the chair condition storage unit according to the exemplary embodiment.

FIG. 11 illustrates an example of the chair conditions in the sitting motion duration stored in the chair condition storage unit 108. In the chair condition storage unit 108, a myoelectric pattern generated when a person is sitting down on each of the types of chairs is stored as the chair condition for the type in the sitting motion duration. The myoelectric pattern is a pattern expressed by using the RMS of the myoelectric potential of each of the muscles. For example, for each of a wooden hard chair (type 1), a soft chair with casters, such as an office chair, (type 2), and a softer and low seat chair, such as a sofa, (type 3), the chair condition storage unit 108 stores, as the chair condition, the myoelectric pattern generated when a person sits down in the chair.

As described above, the chair identifying unit 107 calculates the RMS of the myoelectric potentials of each of the muscles in the entire sitting motion duration. Thereafter, the chair identifying unit 107 identifies the type of chair associated with, among the myoelectric patterns serving as the above-described chair conditions, the myoelectric pattern most similar to the pattern expressed by the calculated RMSs of the myoelectric potentials of the muscles. To calculate the similarity between a set of the measured RMSs of the myoelectric potentials of the muscles and the stored set of the RMSs of the myoelectric potentials corresponding to each of the types of chairs, the following technique, for example, is used. The measured myoelectric potentials and the myoelectric potentials corresponding to each of the types of chairs are expressed in the form of vectors first. For example, when the myoelectric potentials at five portions are measured, the myoelectric potentials are expressed as a five-dimensional vector having elements each being the RMS of the myoelectric potential of one of the muscles. The cosine similarity (the cosine distance) is calculated between the vector made from the measured myoelectric potentials and the vector made from the myoelectric potentials corresponding to each of the types of chairs. The similarity increases with increasing calculation result. Thus, the type of chair is identified. In this manner, the type of chair used in the sitting motion duration is identified.

Note that the myoelectric pattern corresponding to each of the types of chairs stored in the chair condition storage unit 108 may be created by calibration. That is, the myoelectric pattern corresponding to the target type of chair is created by causing the user to sit down in a chair of the target type. Alternatively, the myoelectric pattern corresponding to the target type of chair may be created by causing each of a plurality of persons to sit down in a chair of the target type and averaging the RMSs obtained at that time.

Furthermore, in addition to identifying the type of chair in the sitting motion duration as described above, the chair identifying unit 107 identifies the type of chair in which the user is sitting by using a particular motion performed by the user in the sitting duration. For example, a user sitting in a chair with a caster can move back and forth in the sitting duration. Thus, movement of the legs of the user to move the chair back and forth occurs. Accordingly, by detecting the movement of the legs as the particular motion, the chair identifying unit 107 can identify that the chair in which the user is sitting is a chair with casters.

Figure 12:
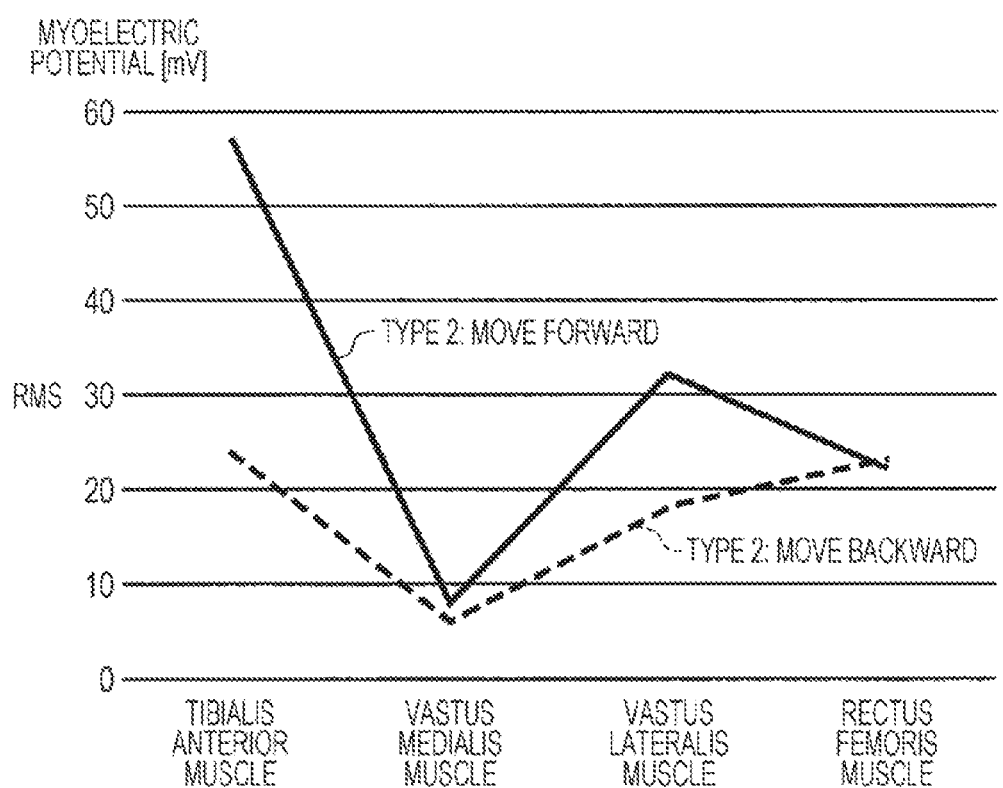
FIG. 12 illustrates an example of a chair condition for a sitting duration stored in the chair condition storage unit according to the exemplary embodiment.

FIG. 12 illustrates an example of the chair conditions in the sitting duration stored in the chair condition storage unit 108. The chair condition storage unit 108 stores, for each of the types of chairs, a myoelectric pattern corresponding to a particular motion performed when a person is sitting in a chair of that type as a chair conditions in the sitting duration. In FIG. 12, the myoelectric patterns corresponding to two types of particular motions are generated while a person is sitting in a chair with a caster (that is, a type-2 chair). One of the two types of myoelectric patterns is a myoelectric pattern generated when the chair is being moved forward, and the other myoelectric pattern is a myoelectric pattern generated when the chair is being moved backward. If one of these particular motions is detected, it is determined that the user is sitting in a chair with casters. Note that the RMS in FIG. 12 is the RMS of the myoelectric potential measured during a predetermined time period from the time the particular motion is detected (a motion identification duration). The time when the particular motion starts is predefined as, for example, a time when at least one of the RMSs of the plurality of muscles calculated at predetermined intervals (for example, 10 ms) in a sitting duration exceeds a threshold value. An RMS calculation duration is defined as a predetermined time period from the start of the particular motion (for example, 500 ms).

The chair identifying unit 107 performs processing for detecting the start of the particular motion on the measurement data acquired after the sitting motion duration and stored in the measurement data storage unit 104. If the start of the particular motion is detected, the chair identifying unit 107 calculates the RMS of the myoelectric potential of each of the muscles in the motion identification duration from the detection time until the predetermined time elapses. Thereafter, the chair identifying unit 107 generates vectors from the chair conditions each corresponding to one of the types of chairs and stored in the chair condition storage unit 108. In addition, the chair identifying unit 107 generates a vector from the calculated RMSs of the myoelectric potentials of the muscles in a manner similar to the above-described manner. Subsequently, the chair identifying unit 107 calculates the cosine similarity of a vector generated from the myoelectric potential of each of the particular motions stored in the chair identifying unit 107. If the similarity is less than or equal to a predetermined value, the motion is none of the particular motions and, thus, the type of chair is not identified. However, if the similarity is higher than or equal to the predetermined value, a particular motion having the highest similarity is selected and determines which one of the types of chairs the particular motion corresponds to. For example, if the most similar myoelectric pattern is the myoelectric pattern illustrated in FIG. 12, the chair identifying unit 107 identifies the type of chair in which the user is sitting as a chair with casters (i.e., type 2).

Figure 13:
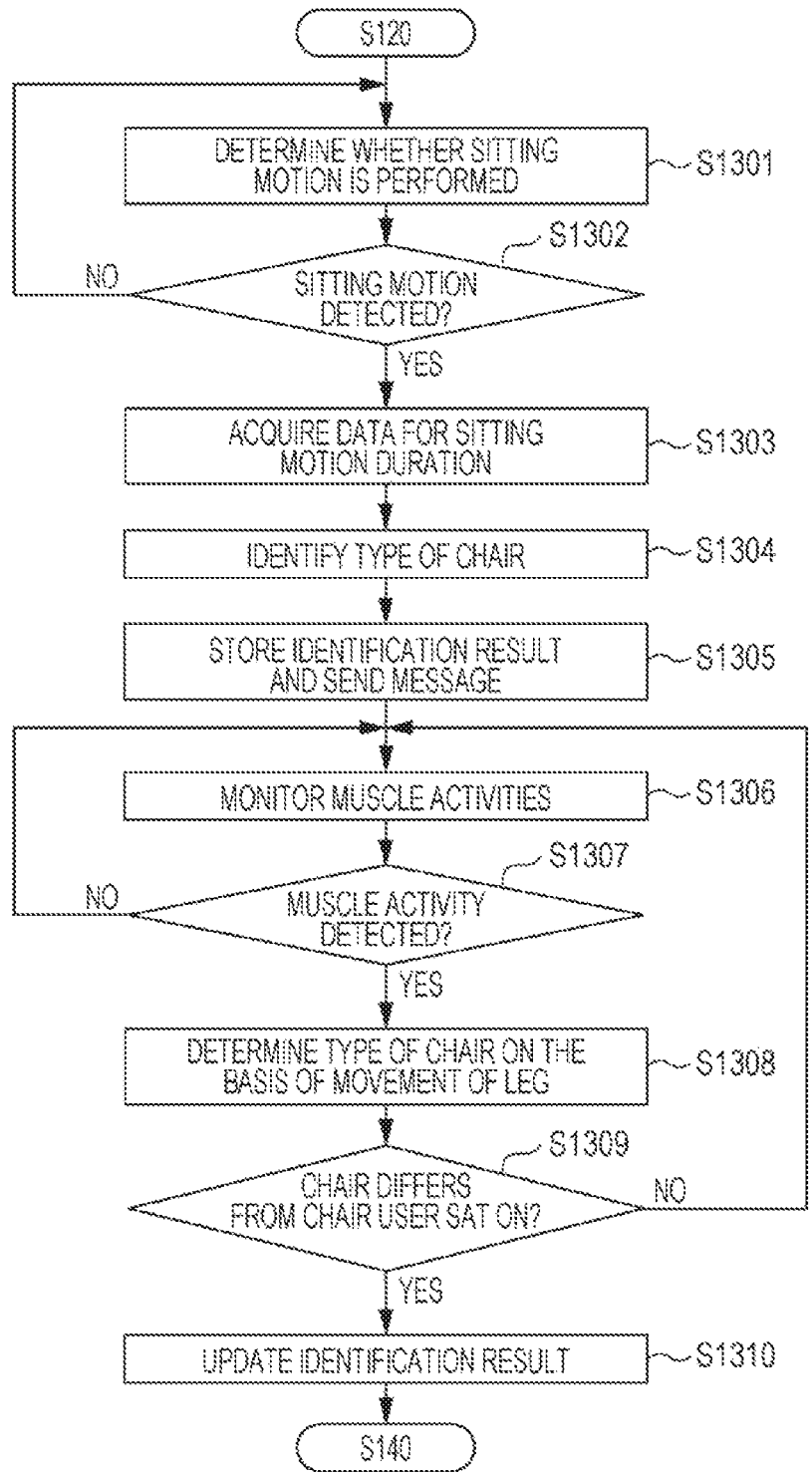
FIG. 13 is a flowchart of a technique for identifying the type of chair by using myoelectric potentials according to the exemplary embodiment.

FIG. 13 is a flowchart of a technique for identifying the chair type by using myoelectric potentials. Note that this flowchart illustrates the details of the processing in step S130 illustrated in FIG. 3.

Step S1301

The chair identifying unit 107 periodically determines whether the sitting detection information transmitted from the sitting motion detection unit 105 has been received.

Step S1302

If the chair identifying unit 107 has received the sitting detection information, the processing proceeds to step S1303. However, if the chair identifying unit 107 has not received the sitting detection information, the processing returns to step S1301 and waits for receipt of the sitting detection information.

Step S1303

The chair identifying unit 107 identifies the sitting motion duration from the sitting detection information received from the sitting motion detection unit 105 and acquires the data in the sitting motion duration from the measurement data stored in the measurement data storage unit 104.

Step S1304

The chair identifying unit 107 compares the pattern represented by the RMS of the myoelectric potential of at least one of the muscles indicated by the data in the sitting motion duration acquired in step S1303 with the myoelectric pattern of each of the types of chairs stored in the chair condition storage unit 108. Through the comparison, the chair identifying unit 107 identifies the type of chair in which the user is sitting down.

Step S1305

The chair identifying unit 107 stores, in the identification result storage unit 109, the type of chair identified in step S1304 as an identified result and sends, to the standing motion detection unit 110, a message indicating that the identified result has been stored.

Step S1306

The chair identifying unit 107 starts the process of identifying the type of chair in which the user is sitting after the sitting motion duration ends. The chair identifying unit 107 periodically (for example, at intervals of 10 ms) acquires, from the measurement data stored in the measurement data storage unit 104, the data measured during the interval (that is, the measurement result of the myoelectric potential of each of the muscles) first. Thereafter, the chair identifying unit 107 calculates the RMS of the myoelectric potential of each of the muscles. That is, the chair identifying unit 107 monitors the muscle activities.

Step S1307

The chair identifying unit 107 determines that the muscle activity has occurred if the RMS of any one of the muscles calculated in step S1306 is greater than the threshold value. In this case, the processing proceeds to step S1308. However, if the chair identifying unit 107 determines that the muscle activity has not occurred, the processing returns to step S1306, where the next RMS is calculated.

Step S1308

If, in step S1307, the chair identifying unit 107 determines that at least one of the muscles has been activated, the chair identifying unit 107 calculates the RMS of the myoelectric potential of each of the muscles in the target duration. That is, the chair identifying unit 107 calculates the RMS of the myoelectric potential of each of the muscles in the target duration from the earliest measurement time of the sample duration until the time after a predetermined elapses among the data used for calculating the RMS of the myoelectric potential that exceeded the threshold value in step S1307. The chair identifying unit 107 compares the pattern represented by the calculated RMS of the myoelectric potential of the muscles with the myoelectric pattern stored in the chair condition storage unit 108 as the chair condition and associated with each of the types of chairs. In this manner, the chair identifying unit 107 identifies the type of chair used in the sitting duration.

Step S1309

The chair identifying unit 107 compares the type of chair identified in step S1308 with the type of chair stored in the identification result storage unit 109 as the identification result.

Step S1310

If, as a result of the comparison, the types of chairs differ from each other, the chair identifying unit 107 updates the type of chair stored in the identification result storage unit 109 as the identification result to the type of chair identified in step S1308. Note that the chair identifying unit 107 may update the identification result a plurality of times by repeatedly performing the processing in step S1306 and the subsequent steps after the processing of the step S1310 is completed.

Method for Identifying Type of Chair by Using Acceleration and Trunk Forward Inclination Angle A method for identifying the type of chair by using the acceleration acquired by the nine-axis sensor and the trunk forward inclination angle is described below.

In this identifying method, the chair identifying unit 107 identifies the type of chair by using two characteristics. One of the two characteristics is that the height of the seat or the hardness of the seat differs according to the type of chair and, thus, the measurement result of the acceleration during the sitting motion differs according to the type of chair. The other characteristic is that the acceleration while the user is sitting differs according to the type of chair, since the angle of the backrest differs according to the type of chair and the work done by the user after sitting in the chair varies from user to user.

Figure 14:
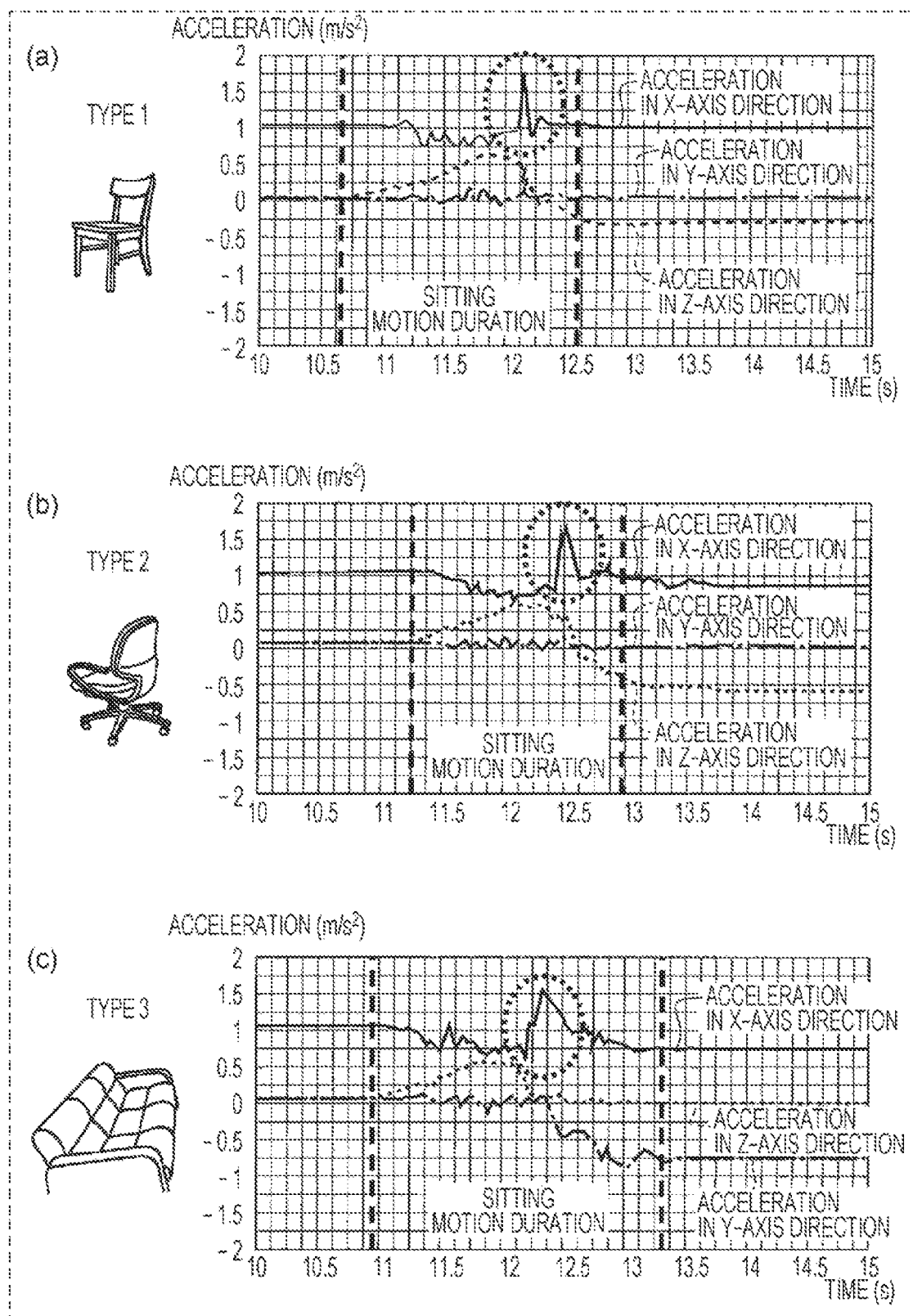
FIG. 14 illustrates an example of the acceleration measured when a user sits down in each of three types of chairs.

FIG. 14 illustrates an example of the acceleration measured when the user sits down in each of the three types of chairs. As illustrated in FIGS. 14(*a*) to 14(*c*), for any type of chair, a large change appears in the acceleration in the x-axis direction (the vertical direction) in the latter half of the sitting motion duration. This change indicates that the direction of acceleration is reversed when the buttocks of the user accelerating in the vertically downward direction are brought into contact with the seat of the chair. As illustrated in FIGS. 14(*a*) to 14(*c*), the change differs according to the type of chair. The reason is that the hardness of the seat of the chair influences the acceleration. The change is more abrupt with increasing hardness of the chair.

Accordingly, in the sitting motion duration, if the vertical upward acceleration is greater than or equal to a threshold value, the chair identifying unit 107 calculates the abruptness of the change in acceleration, that is, the value of the slope of the acceleration. Thereafter, the chair identifying unit 107 identifies the type of chair by comparing the value of the slope with the chair condition (for example, the threshold value) stored in the chair condition storage unit 108 for each of the types of chairs. Note that the value of the slope of the acceleration corresponds to the rate of change of the acceleration. Accordingly, the chair identifying unit 107 may determine the type of chair on the basis of the maximum rate of change of the acceleration in the vertical direction in the sitting motion duration. The chair condition storage unit 108 stores, for example, a condition that the maximum rate of change of the acceleration is greater than or equal to a threshold value a1 for a chair of type 1 and a condition that the maximum rate of change of the acceleration is less than the threshold value a1 and greater than or equal to a threshold value a2 for a chair of type 2. The chair condition storage unit 108 further stores a condition that the maximum rate of change of the acceleration is less than the threshold value a2 for a chair of type 3. For example, if the calculated maximum rate of change of the acceleration is greater than or equal to the threshold value a1, the chair identifying unit 107 identifies the type of chair as "type 1".

As described above, when, in the data measured during the first duration (that is, the sitting motion duration), the vertical acceleration of the upper body of the user is represented as a numerical value according to the posture, the chair identifying unit 107 calculates the maximum rate of change of the acceleration of the upper body of the user during a predetermined time period from the start of the sitting motion and identifies the type of chair in accordance with the calculated maximum rate of change. As a result, the reliability of identifying the type of chair can be increased more.

In addition, the height of the seat of a chair differs according to the type of chair. Accordingly, the movement distance of the waist of the user at the time of the sitting motion differs according to the type of chair. Thus, the chair identifying unit 107 may calculate the movement distance by integrating the vertical acceleration over the sitting motion duration and compare the calculated movement distance with the chair condition stored in the chair condition storage unit 108 for each of the types of chairs. In this manner, the chair identifying unit 107 may identify the type of chair.

In other words, when the acceleration in the vertical direction of the upper body of the user is indicated by the data measured during the first duration in the form of the numerical value corresponding to the posture, the chair identifying unit 107 calculates a movement distance of the upper body of the user in the vertical direction on the basis of the acceleration of the upper body of the user for a period until the acceleration in the vertical upward direction is greater than or equal to the threshold value. Thereafter, the chair identifying unit 107 identifies the type of chair in accordance with the movement distance. As a result, the reliability of identifying the type of chair can be increased more. Note that, in this case, the chair condition storage unit 108 stores, as the chair condition, the above-described acceleration threshold value and the movement distance threshold value associated with each of the plurality of types of chairs. The chair identifying unit 107 compares the calculated movement distance with the threshold of the movement distance, which is the chair condition, and identifies the type of chair on the basis of the comparison result.

In addition, the minimum value of the trunk forward inclination angle of a user at the time of sitting motion differs according to the type of chair. For example, when the user sits down in a low seat chair or a deep chair, the trunk of the user leans forward more. Accordingly, the minimum value of the trunk forward inclination angle decreases. In contrast, when the user sits down in a chair with a high seat height or a chair in front of a desk, the trunk of the user does not largely lean forward, such that the minimum value of the trunk forward inclination angle is large. Accordingly, the chair identifying unit 107 may calculate the trunk forward inclination angle by integrating the angular velocity around the y-axis (the rotation center) in the sitting motion duration. Thereafter, the chair identifying unit 107 may compare the calculated trunk forward inclination angle with the chair condition (for example, the threshold value) stored in the chair condition storage unit 108 for each of the types of chairs. In this manner, the chair identifying unit 107 may identify the type of chair.

In addition, the inclination angle of the backrest of the chair differs according to the type of chair. Accordingly, when the user remains sitting in a chair, that is, in the sitting duration, the chair identifying unit 107 periodically calculates the trunk forward inclination angle on the basis of the angular velocity measured by the nine-axis sensor. Thereafter, the chair identifying unit 107 compares the maximum value of the periodically calculated trunk forward inclination angles with the chair condition (for example, the threshold value) stored in the chair condition storage unit 108 for each of the types of chairs. In this manner, the chair identifying unit 107 identifies the type of chair in which the user is sitting.

FIG. 15 illustrates another example of the chair condition in the sitting duration stored in the chair condition storage unit 108. The chair condition storage unit 108 stores, as a chair condition corresponding to a type of chair, a threshold value of the trunk forward inclination angle for each of the types of chairs. For example, the chair condition storage unit 108 stores a threshold value of 110 deg of the trunk forward inclination angle as the chair condition for a type-1 chair, and a threshold value of 120 deg of the trunk forward inclination angle as the chair condition for a type-2 chair. Furthermore, the chair condition storage unit 108 stores a threshold of 130 deg of the trunk forward inclination angle as the chair condition for a type-3 chair.

If the maximum value of the trunk forward inclination angle calculated in the sitting duration is less than or equal to the threshold value of type 1, the chair identifying unit 107 identifies the type of the chair as type 1, If the maximum value is greater than the threshold value of type 1 and less than or equal to the threshold value of type 2, the chair identifying unit 107 identifies the type of the chair as type 2. However, if the maximum value of the trunk forward inclination angle calculated in the sitting duration is greater than the threshold value of type 2 and less than or equal to the threshold value of type 3, the chair identifying unit 107 identifies the type of the chair as type 3.

That is, when the angular velocity of the upper body of the user is included in the data measured during the second duration in the form of a numerical value corresponding to the posture, the chair identifying unit 107 calculates the trunk forward inclination angle of the user from the angular velocity indicated by the data and identifies the type of chair in accordance with the trunk forward inclination angle. As a result, the reliability of identifying the type of chair can be increased more.

Figure 16:
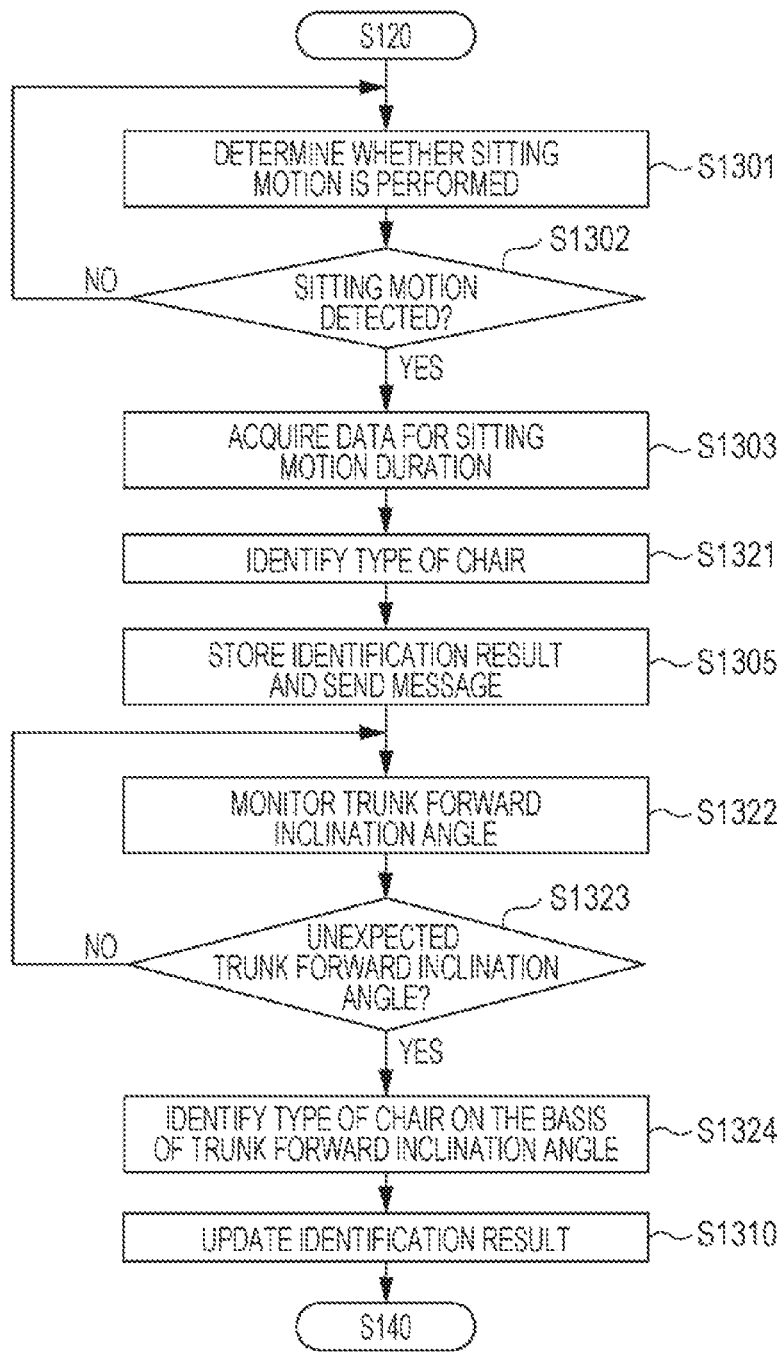
FIG. 16 is a flowchart of a method for identifying the type of chair by using the acceleration and the trunk forward inclination angle according to the exemplary embodiment.

Note that the chair identifying unit 107 may identify the type of chair on the basis of the period of time during which the calculated trunk forward inclination angle is continuously smaller than 90 deg. When a desk is placed in front of the chair and the user is working on the desk, the period of time during which the user continuously maintains the forward-leaning posture differs according to the height of the desk. Accordingly, for example, if the period of time during which a small trunk forward inclination angle is continuously maintained is long, the chair identifying unit 107 identifies the type of chair as an office chair. However, if the period of time during which a small trunk forward inclination angle is continuously maintained is short, the chair identifying unit 107 identifies the type of chair as a sofa, FIG. 16 is a flowchart of a method for identifying the type of chair by using the acceleration and the trunk forward inclination angle. Note that this flowchart illustrates the details of the processing performed in step S130 illustrated in FIG. 3, Step S1301

The chair identifying unit 107 periodically determines whether the sitting detection information transmitted from the sitting motion detection unit 105 has been received.

Step S1302

If the chair identifying unit 107 has received the sitting detection information, the processing proceeds to step S1303. However, if the chair identifying unit 107 has not received the sitting detection information, the processing returns to step S1301, where the chair identifying unit 107 waits for receipt of the sitting detection information.

Step S1303

The chair identifying unit 107 identifies a sitting motion duration by using the sitting detection information received from the sitting motion detection unit 105 and acquires data measured in the sitting motion duration from the measurement data stored in the measurement data storage unit 104.

Step S1321

The chair identifying unit 107 compares the maximum rate of change of the acceleration in the x-axis direction indicated by the data measured in the sitting motion duration and acquired in step S1303 with the threshold value stored in the chair condition storage unit 108 for each of the types of chairs. Through the comparison, the chair identifying unit 107 identifies the type of chair in which the user sits down. Note that the chair identifying unit 107 may calculate the minimum value of the trunk forward inclination angle on the basis of at least one angular velocity indicated by the data. Thereafter, the chair identifying unit 107 may compare the calculated minimum value of the trunk forward inclination angle with the threshold value of the trunk forward inclination angle and identify the type of chair.

Step S1305

The chair identifying unit 107 stores, in the identification result storage unit 109, the type of chair identified in step S1321 as the identified result and sends, to the standing motion detection unit 110, a message indicating that the identification result has been stored.

Step S1322

The chair identifying unit 107 starts the process of identifying the type of chair when the user remains sitting after the sitting motion duration ends. The chair identifying unit 107 periodically acquires, from the measurement data stored in the measurement data storage unit 104, the data measured during the period (that is, the measurement result of the nine-axis sensor) first. Thereafter, the chair identifying unit 107 calculates the trunk forward inclination angle on the basis of the data measured during the period. That is, the chair identifying unit 107 monitors the trunk forward inclination angle.

Step S1323

The chair identifying unit 107 determines whether the trunk forward inclination angle calculated in step S1322 is inconsistent with the trunk forward inclination angle expected from the type of chair identified in step S1321. In other words, the chair identifying unit 107 determines whether the trunk forward inclination angle calculated in step S1322 is unexpected. More specifically, when the type of chair identified in step S1321 is type 1 (a wooden chair illustrated in FIG. 15), the chair identifying unit 107 acquires the threshold value of the trunk forward inclination angle corresponding to type 1 (100 deg) from the chair condition storage unit 108. In this example, if, in step S1322, the trunk forward inclination angle greater than 100 deg is calculated or the trunk forward inclination angle of about 70 deg is continuously calculated for the predetermined period of time or longer, the chair identifying unit 107 determines that the calculated trunk forward inclination angle is unexpected. When the chair identifying unit 107 determines that the calculated trunk forward inclination angle is unexpected, the processing proceeds to step S1324. However, if it is determined that the calculated trunk forward inclination angle is not unexpected, the chair identifying unit 107 repeatedly performs the processing in step S1322 and the subsequent steps (that is, monitoring the trunk forward inclination angle). Note that the chair identifying unit 107 stops the monitoring process in step S1322 when the standing motion detection unit 110 detects a standing motion.

Step S1324

The chair identifying unit 107 compares the unexpected trunk forward inclination angle calculated in step S1322 with the threshold of the trunk forward inclination angle stored in the chair condition storage unit 108 for each of the types of chairs. In this manner, the chair identifying unit 107 identifies the type of chair.

Step S1310

The chair identifying unit 107 updates the type of chair stored in the identification result storage unit 109 as the identification result to the type of chair identified in step S1324.

Standing Motion Detection Unit

If, in step S140 illustrated in FIG. 3, the standing motion detection unit 110 receives, from the chair identifying unit 107, the message indicating that the identified result of the type of chair has been stored in the identification result storage unit 109, the standing motion detection unit 110 detects the start of the standing motion after receiving the message. That is, the standing motion detection unit 110 detects the start of the standing motion by using the measurement data stored in the measurement data storage unit 104 for the user.

At this time, to more effectively assist the user with a standing motion, the standing motion detection unit 110 may detect the standing motion at the earliest possible time. For example, in the case of detecting the standing motion by the change in the acceleration in the vertical direction, since the change in the acceleration caused by the standing motion is directly measured, the time of the standing motion is inevitably after the start of the standing motion. Thus, assistance is delayed.

In view of such a situation, according to the present exemplary embodiment, the standing motion detection unit 110 detects the standing motion on the basis of the trunk forward inclination motion performed before the standing motion is performed (that is, before the buttocks are lifted from the seat of the chair) and the activities of the muscles of the lower limbs caused by the trunk forward inclination motion.

Figure 17:
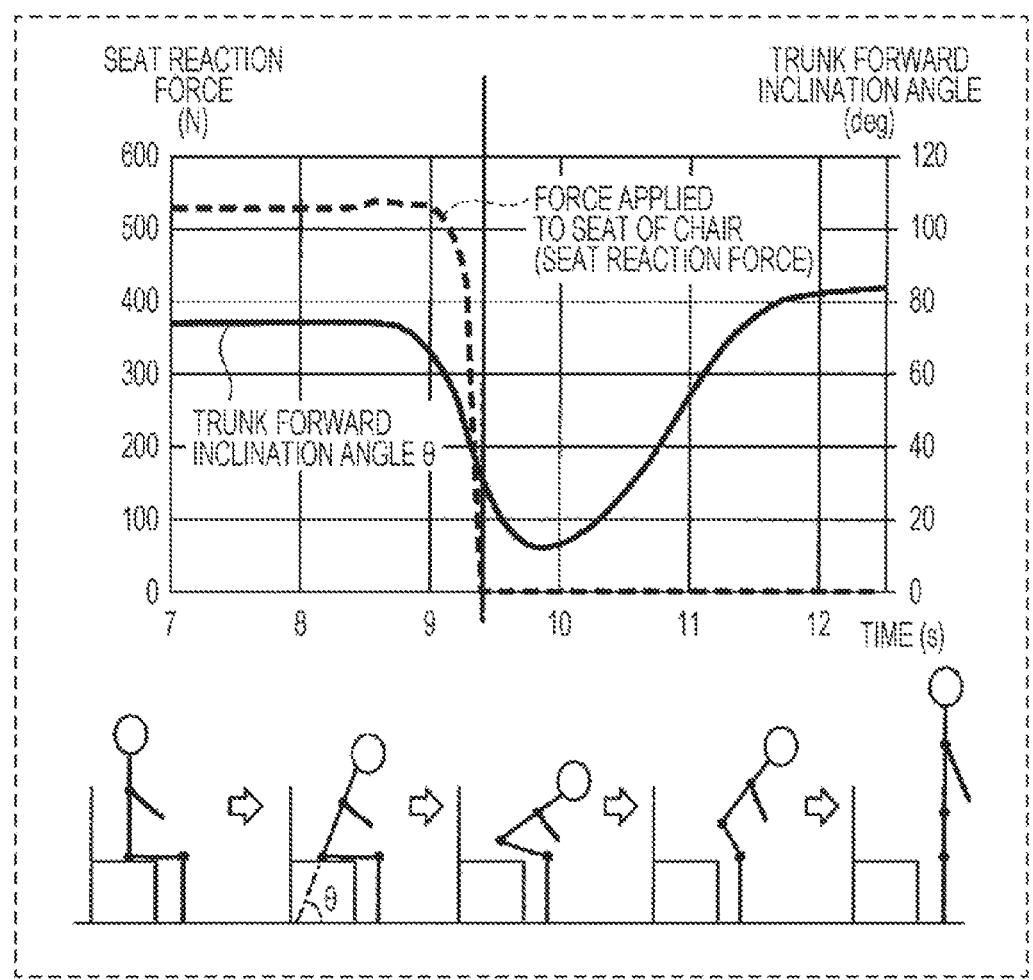
FIG. 17 illustrates an example of the trunk forward inclination angle calculated when a user stands up.

FIG. 17 illustrates an example of the trunk forward inclination angle calculated when the user stands up. As illustrated in FIG. 17, when the user stands up, the trunk forward inclination angle is about to decrease due to the trunk forward inclination motion of the user first. While the trunk forward inclination angle is decreasing, the force applied to the seat (known as a "seat reaction force") abruptly decreases to 0. That is, after the trunk front inclination angle begins to decrease, the buttocks are lifted from the seat. Accordingly, when the trunk forward inclination angle decreases, it is highly likely that the standing motion starts.

Accordingly, the standing motion detection unit 110 periodically calculates the most recent trunk forward inclination angle on the basis of the angular velocity about the y-axis indicated by the measurement data stored in the measurement data storage unit 104. Thereafter, the standing motion detection unit 110 determines whether the calculated trunk forward inclination angle is less than or equal to a threshold value of the trunk forward inclination angle stored in the standing condition storage unit 111 as the standing condition.

If the calculated trunk forward inclination angle is less than or equal to the threshold value, the standing motion detection unit 110 further monitors the activities of the muscles of the lower limbs.

More specifically, among the measurement data stored in the measurement data storage unit 104, the standing motion detection unit 110 references data of the sample having a measurement time that is a predetermined time prior to the time at which the trunk forward inclination angle reaches the threshold value or less to the sample having the most recent measurement time. Thereafter, the standing motion detection unit 110 determines whether the muscles have started their activities in a predetermined order by using the data. More specifically, for example, the standing motion detection unit 110 performs full-wave rectification and low-pass filtering on the myoelectric potential at each of the times indicated by the data for each of the muscles to be measured and, thus, ARV (Average Rectified Value) is calculated at each time. Thereafter, when the calculated ARV reaches a value greater than or equal to a threshold value of the ARV stored as the standing condition in the standing condition storage unit 111, the standing motion detection unit 110 determines that the muscle has started its activity. The standing motion detection unit 110 stores the time when it is determined that each of the muscles to be measured has started its activity and obtains the order in which the muscles have started their activities.

Figure 18:
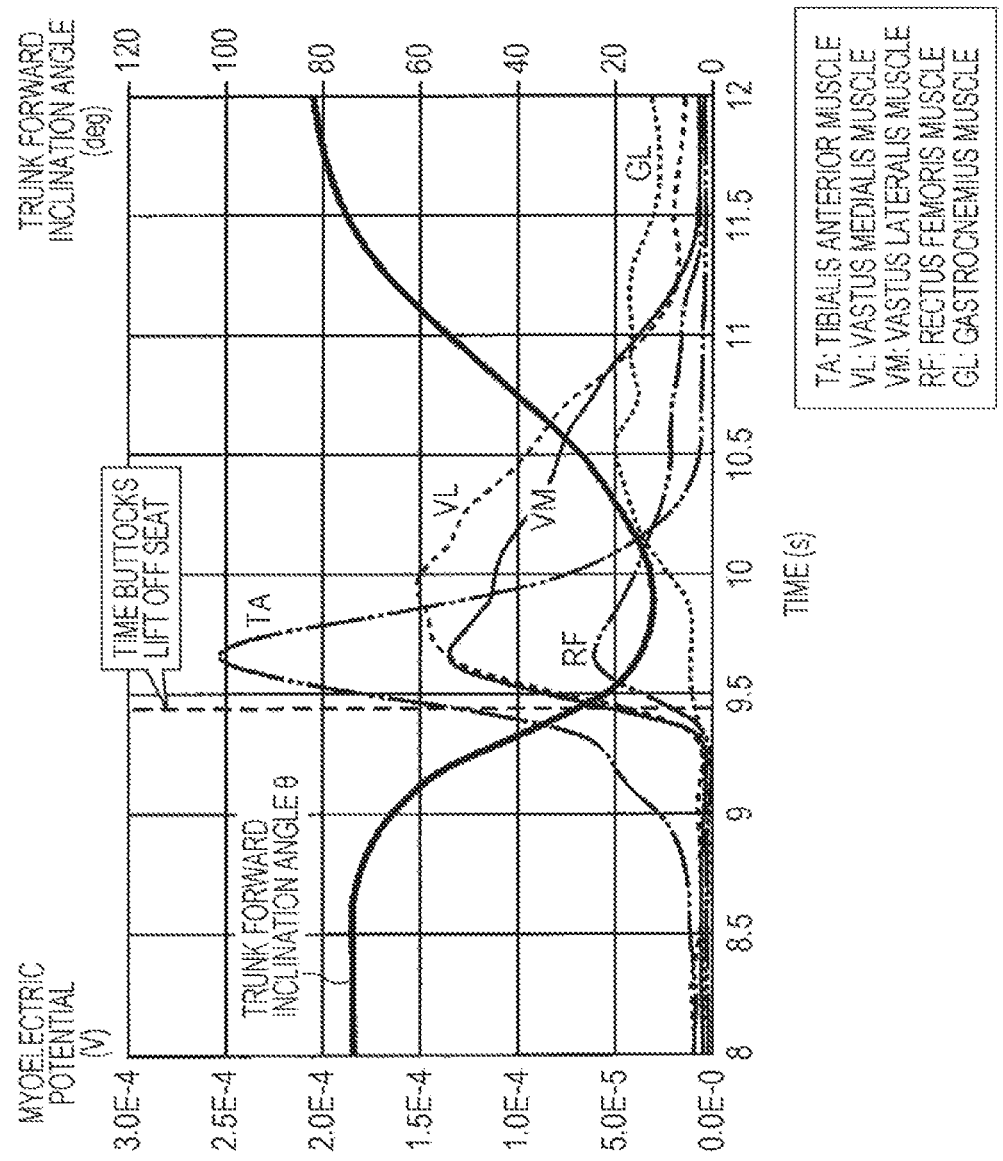
FIG. 18 illustrates an example of the ARV of the myoelectric potential measured for each of the muscles while the standing motion is being performed.

FIG. 18 illustrates an example of the ARV of the myoelectric potential measured for each of the muscles while the standing motion is being performed. As illustrated in FIG. 18, the activity start times of the muscles differ from one another. The standing motion detection unit 110 detects the start of the standing motion by using the order in which the muscles have started their activities. More specifically, as illustrated in FIG. 18, when the standing motion is started, the tibialis anterior muscle (TA in FIG. 18) is activated first. Subsequently, the vastus medialis muscle (VL in FIG. 18) and the vastus lateralis muscle (VM in FIG. 18) are activated at substantially the same time. Subsequently, the rectus femoris muscle (RF in FIG. 18) and the gastrocnemius muscle (GL in FIG. 18) are activated.

Accordingly, the standing condition storage unit 111 according to the present exemplary embodiment stores, as the standing condition, the order in which the muscles starts their activities, that is, the tibialis anterior muscle starts its activity first and, thereafter, the vastus medialis muscle starts its activity. Accordingly, when the tibialis anterior muscle starts its activity and, thereafter, the medial broad muscle starts its activity, the standing motion detection unit 110 determines that the order of the activities meets the standing condition. That is, the standing motion detection unit 110 detects the start of the standing motion of the user at this time.

As described above, when the myoelectric potentials of a plurality of muscles in the legs of the user are indicated by the measurement data, the standing motion detection unit 110 detects the order in which the plurality of muscles start their activities on the basis of the myoelectric potentials of the muscles in the leg after the sitting motion indicated by the measurement data. If the identified order is the same as a predetermined order, the standing motion detection unit 110 detects the start of the standing motion. As a result, the start of the standing motion can be detected at an appropriate point in time. In addition, when the measurement data further indicates the angular velocity of the upper body of the user in the form of a numerical value corresponding to the posture of the user, the standing motion detection unit 110 calculates the trunk forward inclination angle of the user from the angular velocity indicated by the measurement data. If the trunk forward inclination angle reaches a value less than or equal to the threshold value, the standing motion detection unit 110 determines the order in which the muscles start their activities. In this manner, the start of the standing motion can be detected at a more appropriate point in time.

Furthermore, the standing condition storage unit 111 may store, as the standing condition, a condition that the ARV of the tibialis anterior muscle is larger than the ARV of the medial broad muscle at the time when the medial broad muscle starts its activity. In this case, the standing motion detection unit 110 may compare the ARV of the tibialis anterior muscle with the ARV of the vastus medialis muscle when the vastus medialis muscle starts its activity. If the ARV of the tibialis anterior muscle is larger, it may be determined that the greater-lesser relationship of ARV meets the standing condition. At this time, the standing motion detection unit 110 detects the start of the standing motion of the user.

Figure 19:
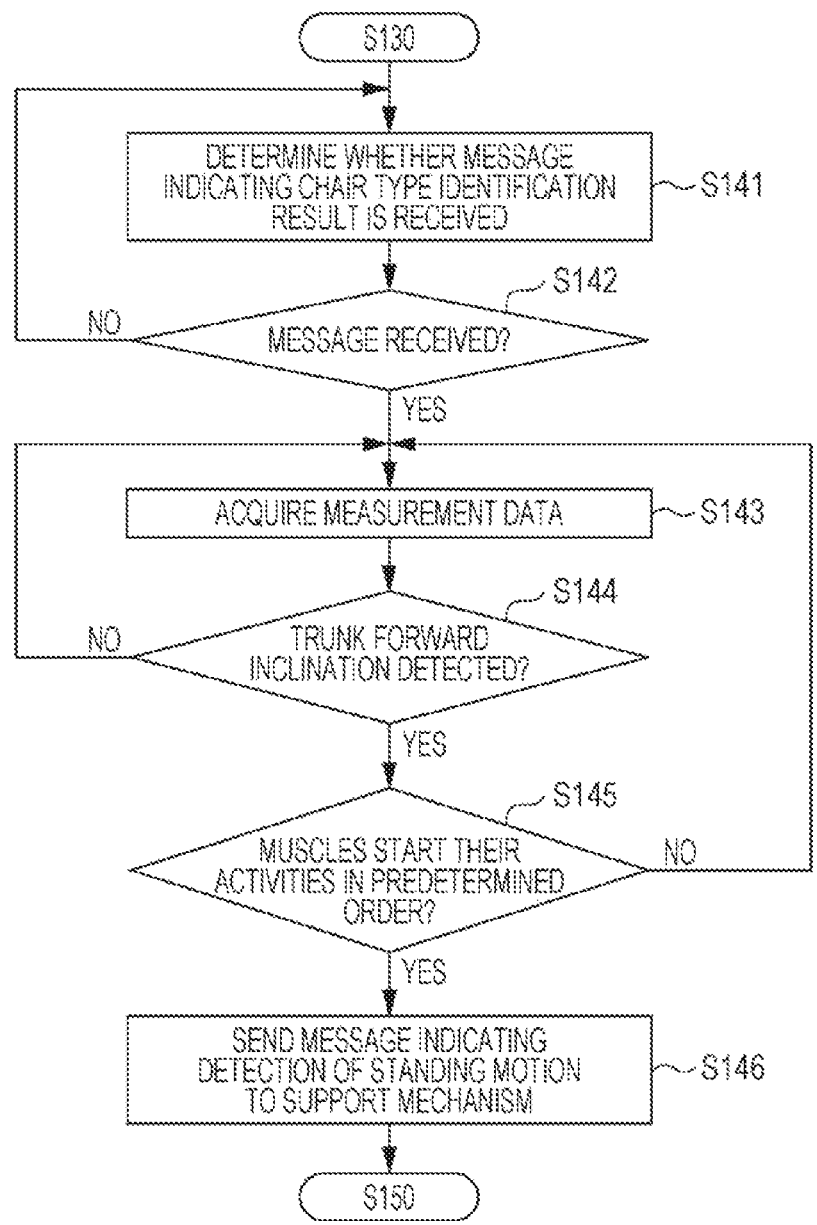
FIG. 19 is a flowchart of the detailed process performed by a standing motion detection unit according to the exemplary embodiment.

FIG. 19 is a flowchart of the detailed processing performed by the standing motion detection unit 110. Note that this flowchart illustrates the detailed processing in step 3140 illustrated in FIG. 3.

Step S141

The standing motion detection unit 110 periodically determines whether the message indicating that the identification result of the type of chair has been stored has been received from the chair identifying unit 107.

Step S142

If, as a result of determination in step S141, the standing motion detection unit 110 has not received the message, the processing returns to step S141. However, if the standing motion detection unit 110 has received the message, the processing proceeds to step S143.

Step S143

The standing motion detection unit 110 acquires the identification result from the identification result storage unit 109. In addition, the standing motion detection unit 110 periodically acquires the most recent sample from the measurement data stored in the measurement data storage unit 104.

Step S144

The standing motion detection unit 110 calculates the trunk forward inclination angle of the user on the basis of the angular velocity around the y-axis indicated by the successively acquired sample. At this time, if the user largely leans forward and, thus, the trunk forward inclination angle reaches a value less than or equal to the threshold value, the processing proceeds to step S145. However, if the trunk forward inclination angle has not reached the value less than or equal to the threshold value, the processing returns to step 143, where the standing motion detection unit 110 continuously acquires the sample. Note that the above-mentioned threshold value is stored in the standing condition storage unit 111 as the standing condition.

Step S145

As described above, among the measurement data stored in the measurement data storage unit 104, the standing motion detection unit 110 references data of the samples having a measurement time that is a predetermined time prior to the time at which the trunk forward inclination angle reaches the threshold value or less to the sample having the most recent measurement time. Thereafter, the standing motion detection unit 110 uses the data to determine whether the muscles have started their activities in a predetermined order. If the standing motion detection unit 110 determines that the muscles have started their activities in the predetermined order, the processing proceeds to the step S146. However, if the standing motion detection unit 110 determines that the muscles have not started their activities in the predetermined order, the standing motion detection unit 110 repeatedly performs the processing in step S143 and the subsequent steps.

Step S146

Upon determining that the muscles have started their activities in the predetermined order in step S145, the standing motion detection unit 110 sends, to the support mechanism 112, a message that the start of the standing motion has been detected.

In step S146, the standing motion detection unit 110 sends a message indicating that the start of the standing motion has been detected and acquires the type of chair stored in the identification result storage unit 109 as the identification result. Thereafter, the standing motion detection unit 110 references the assist information associated with each of the type of chairs stored in the assist information storage unit 113 and sends the assist information associated with the acquired type of chair to the support mechanism 112. The support mechanism 112 assists the user with the standing motion by driving the power unit 112c on the basis of the assist information.

Figure 20:
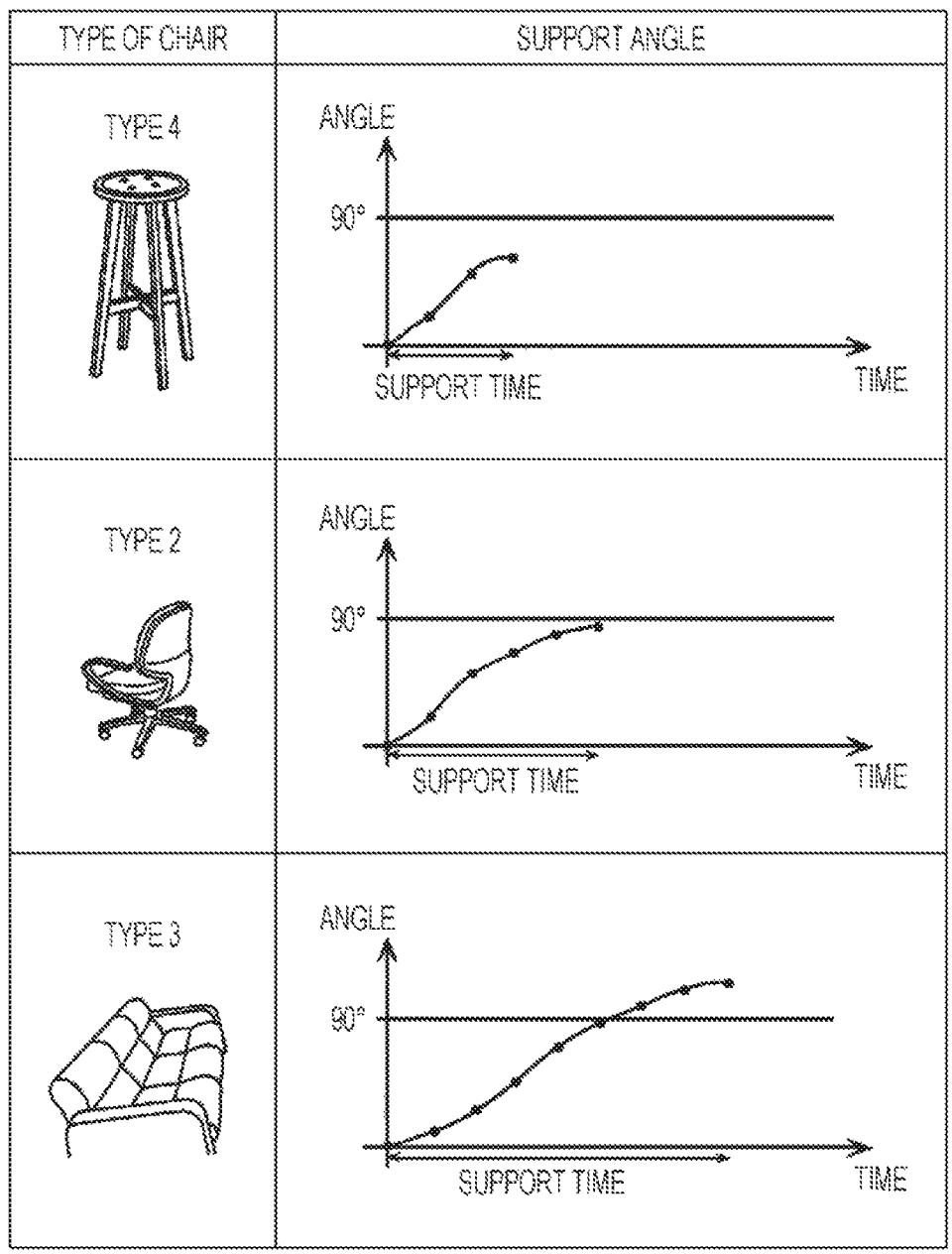
FIG. 20 illustrates an example of the assist information associated with each of the types of chairs stored in an assist information storage unit according to the exemplary embodiment.

FIG. 20 illustrates an example of the assist information associated with each of the types of chairs stored in the assist information storage unit 113. For example, as illustrated in FIG. 20, the assist information storage unit 113 stores information indicating a change in a support angle over time (that is, a time change) as assist information associated with each type of chair. The support angle is an amount of change in a frame angle ϕ formed by the thigh frame 112a and the shank frame 112b during the standing motion. In other words, the support angle is the angle from a frame angle ϕ1 when the user remains sitting in the chair to a frame angle ϕ2 after the start of assist with a standing motion by the support mechanism 112 (that is, ϕ2-ϕ1). In addition, the time change of the support angle represents the speed of assisting with the standing motion.

More specifically, as illustrated in FIG. 20, the assist information storage unit 113 stores the assist information associated with each of a type-4 chair, a type-2 chair, and a type-3 chair. The type-4 chair is a high hard seat chair. The type-2 chair is a chair with a seat lower and softer than the type-4 chair, such as an office chair. The type-3 chair is a chair with a seat lower and softer than the type-2 chair, such as a sofa which allows the buttocks of the user to readily sink thereinto.

In the type-3 chair, the buttocks of the user readily sink. Accordingly, the frame angle ϕ is small when the user is sitting in the chair. Thus, when assisting the user with the standing motion, the support mechanism 112 needs to change the support angle greatly from 0 deg to greater than 90 deg over a long time until the frame angle ϕ reaches 180 deg. Consequently, the assist information associated with a type-3 chair indicates a time change in the support angle so that the support time in which the support angle changes is long, and the support angle gently increases when support with the standing motion is started and, thereafter, exceeds 90 deg.

In a type-2 chair, the seat is higher than in a type-3 chair, and the frame angle ϕ1 is larger than in the type-3 chair when the user is sitting in the chair. Accordingly, when the support mechanism 112 supports the user with the standing motion, it is not necessary to greatly change the support angle over a long time. Accordingly, the assist information associated with a type-2 chair indicates a time change in the support angle so that the support time is short, the support angle promptly increases when support with the standing motion is started, and the support angle increases up to, for example, about 85 deg.

In a type-4 chair, the seat is higher than in a type-2 chair, and the frame angle ϕ1 when the user is sitting in the chair is greater than in a type-2 chair. Accordingly, when supporting the user with the standing motion, the support mechanism 112 may change the support angle only for a short time. Thus, the assist information associated with a type-4 chair indicates a time change in the support angle so that a support time is shorter than in a type-2 chair, the support angle promptly increases when support with the standing motion is started, and the support angle increases up to, for example, about 60 to 70 deg.

Note that the above-described assist information indicates a time change in the support angle including the support time. The assist information may further indicate the torque of the power unit 112c to increase the frame angle ϕ. For example, the assist information about a type-3 chair indicates a large torque, the assist information about a type-2 chair indicates a small torque, and the assist information about a type-4 chair indicates a torque smaller than the torque for the type-2 chair. Furthermore, the assist information may further indicate the time change in the torque. For example, the assist information indicates a time change in torque so that a large torque is generated when assist with a standing motion is started, and the torque gradually decreases to zero. In addition, the torque at the start of the assistance indicated by the assist information may be large for a type-3 chair, small for a type-2 chair, and even smaller for a type-4 chair.

In this manner, the support mechanism 112 acquires, from the standing motion detection unit 110, the assist information illustrated in FIG. 20, which is associated with the type of chair in which the user is sitting. Thereafter, the support mechanism 112 drives the power unit 112c on the basis of the acquired assist information. As a result, the support mechanism 112 can appropriately support the user with a standing motion.

That is, the standing motion detection unit 110 outputs the assist information used by the support mechanism 112 to change the angle of the knee joints of the user by using the speed or force corresponding to the identified type of chair. In this manner, the user can be assisted with a standing motion so as to extend their knee joints by using the speed or force corresponding to the type of chair.

Note that, in step S143 illustrated in FIG. 19, the standing motion detection unit 110 may acquire the identification result stored in the identification result storage unit 109, that is, the type of chair. In addition, the standing condition storage unit 111 may store, as the standing condition corresponding to each of the types of chairs, the threshold value of the trunk forward inclination angle, the threshold value of the ARV, and the order in which the activities of the muscles start. In this case, in step S144, the standing motion detection unit 110 may read out, from the standing condition storage unit 111, the threshold value corresponding to the type of chair and acquired in step S143 and determine whether the calculated trunk forward inclination angle is greater than or equal to the threshold value. For example, the standing condition storage unit 111 stores 80 deg as the threshold value of the trunk forward inclination angle corresponding to a type-1 chair (a wooden chair) and 60 degrees as the threshold value of the trunk forward inclination angle corresponding to a type-2 chair (an office chair). Furthermore, the standing condition storage unit 111 stores 50 deg as the threshold value of the trunk forward inclination angle corresponding to a type-3 chair (a sofa). That is, the standing motion detection unit 110 changes the threshold value of the trunk forward inclination angle in accordance with the identified type of chair. Since the start of the standing motion is detected on the basis of the chair in which the user is sitting in this manner, the start of the standing motion can be detected highly accurately. Similarly, in step S145, the standing motion detection unit 110 may read out, from the standing condition storage unit 111, the order in which the activities of the muscles corresponding to the type of chair acquired in step S143 start and determine whether the muscle activities start in that order. Even in this case, since the start of the standing motion is detected on the basis of the chair in which the user is sitting, the start of the standing motion can be detected highly accurately.

Effects

As described above, according to the present exemplary embodiment, the type of chair is identified on the basis of the biological value of the user (that is, a numerical value corresponding to the myoelectric potential or the posture) after the start of the sitting motion, and the support mechanism assists the user with a standing motion in accordance with the type of chair. Consequently, an insufficient or excess force applied for assisting the user with a standing motion can be prevented and, thus, the standing motion of the user can be stabilized. As a result, the user can be appropriately assisted with a standing motion. That is, according to the present exemplary embodiment, since the standing motion assist device can support the user with the standing motion by using the force or the speed corresponding to the chair in which the user is sitting, a stable assistance can be provided to the user in a standing motion. In addition, since an excess force is not applied, extra energy is not consumed and, thus, a battery-powered standing motion assist device can be used for a long period of time.

Modification

As illustrated in FIG. 19, according to the above-described exemplary embodiment, the start of the standing motion of the user is detected on the basis of the trunk forward inclination angle and the order in which the muscles start their activities. According to the present modification, the start of the standing motion of the user is detected on the basis of the measured myoelectric potential and the type of chair identified in step S130 illustrated in FIG. 3. The measured myoelectric potential of a muscle is, for example, the myoelectric potential of the tibialis anterior muscle or the biceps femoris muscle. Note that a value indicated as the above-mentioned ARV may be used as the myoelectric potential.

Figure 21:
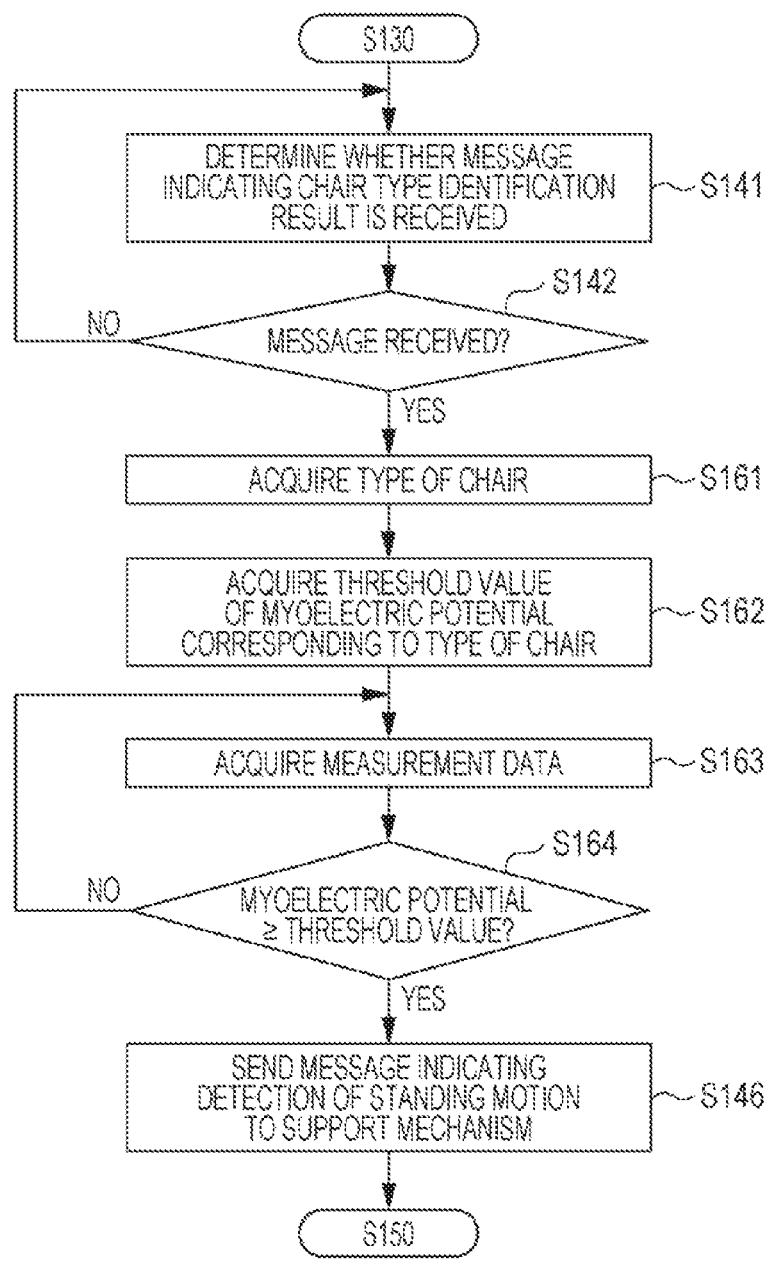
FIG. 21 is a flowchart of the detailed process performed by the standing motion detection unit according to a modification of the exemplary embodiment.

FIG. 21 is a flowchart of the detailed process performed by the standing motion detection unit 110 according to the present modification. Note that this flowchart illustrates the detailed processing performed in step S140 illustrated in FIG. 3.

Step S141

The standing motion detection unit 110 periodically determines whether the message indicating the identification result of the type of chair has been received from the chair identifying unit 107.

Step S142

If, as a result of the determination in step S141, the myoelectric potential measurement unit 101 has not received the message, the processing returns to the step S141. However, if the myoelectric potential measurement unit 101 has received the message, the processing proceeds to the step S161.

Step S161

The standing motion detection unit 110 acquires the identification result stored in the identification result storage unit 109, that is, the type of chair.

Step S162

Subsequently, by referencing the standing condition stored in the standing condition storage unit 111, the standing motion detection unit 110 acquires the identification threshold value, that is, the threshold value of the myoelectric potential corresponding to the type of chair acquired in step S161.

Step S163

Subsequently, the standing motion detection unit 110 periodically acquires the most recent sample from the measurement data stored in the measurement data storage unit 104.

Step S164

Subsequently, the standing motion detection unit 110 determines whether the myoelectric potential of the muscle, such as the tibial anterior muscle or the biceps femoris muscle, indicated by the most recent sample is greater than or equal to the identification threshold value acquired in step S162. If the standing motion detection unit 110 determines that the myoelectric potential of the muscle is greater than or equal to the identification threshold value (Yes in step S164), the processing proceeds to the step S146. However, if the standing motion detection unit 110 determines that the myoelectric potential of the muscle is less than the identification threshold value (No in step S164), the standing motion detection unit 110 repeatedly performs the processing in step S163 and the subsequent steps.

Step S146

If, in step S164, the standing motion detection unit 110 determines that the myoelectric potential of the muscle is greater than or equal to the identification threshold value, the standing motion detection unit 110 sends, to the support mechanism 112, a message that the start of the standing motion has been detected.

FIG. 22 illustrates an example of the standing condition stored in a standing condition storage unit 111 according to the present modification.

As illustrated in FIG. 22, threshold values Th4, Th2 and Th3 of the myoelectric potential associated with the type-4 chair, the type-2 chair, and the type-3 chair, respectively, are stored in the standing condition storage unit 111, As mentioned above, a type-4 chair is a high, hard seat chair. A type-2 chair is a chair with a seat lower and softer than the type-4 chair, such as an office chair. A type-3 chair is a chair with a seat lower and softer than the type-2 chair, such as a sofa which allows the buttocks of the user to readily sink thereinto. That is, the type-4 chair has the highest seat among the above-mentioned all types of chairs, and the type-2 chair has the second highest seat. The type-3 chair has the lowest seat.

Among the myopotential threshold values Th4, Th2 and Th3 stored in the standing condition storage unit 111, the threshold value Th4 associated with a type-4 chair having a high seat height is the smallest, and the threshold value Th2 associated with a type-2 chair is the second smallest. The threshold value Th3 associated with a type-3 chair having a low seat height is the largest.

That is, for each of the plurality of types of chairs, the standing condition storage unit 111 stores a threshold value of the myoelectric potential in association with the type of chair, and the threshold value deceases with increasing seat height of a chair of the type.

As described above, according to the present modification, the standing motion detection unit 110 acquires, as the identification threshold value, the threshold value of the myoelectric potential indicating a value that decreases with increasing seat height of the identified type of chair. Thereafter, if the myoelectric potential of the muscle in the leg of the user is indicated by the measurement data, the standing motion detection unit 110 detects the start of the standing motion if the myoelectric potential of the muscle that occurs after the sitting motion and that is indicated by the measurement data is greater than or equal to the identification threshold value.

In this manner, the start of the standing motion can be detected at an appropriate point in time in accordance with the type of chair in which the user is sitting.

Other Embodiments

While the standing motion assist devices according to one or more aspects have been described above with reference to the exemplary embodiments, the present disclosure is not limited to the exemplary embodiments. A variety of modifications of the present embodiment that are conceivable by those skilled in the art and an embodiment configured by combining constituent elements of different embodiments may be encompassed in the spirit and scope of the present disclosure.

For example, the standing motion support device according to the above exemplary embodiment is a wearable assist device. However, the assist device may be of a non-wearable type.

Figure 23:
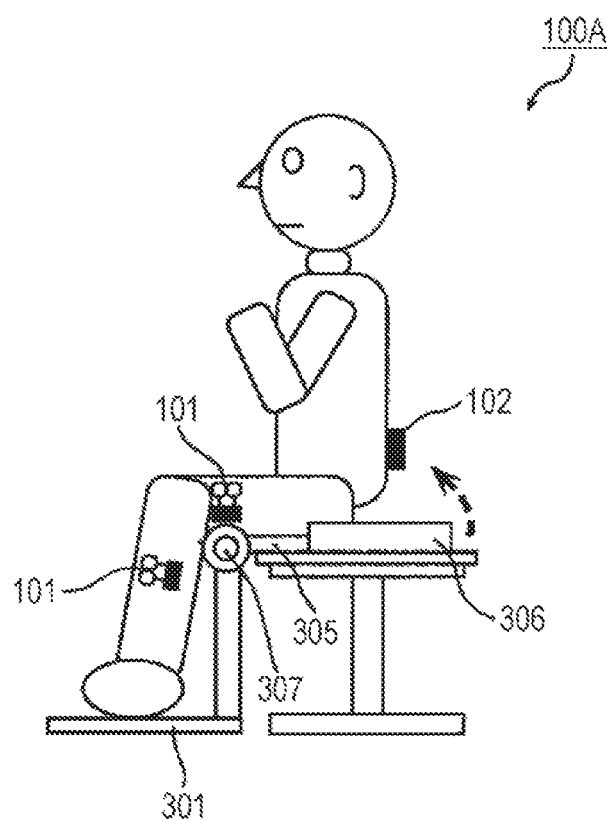
FIG. 23 is an external view of a non-wearable standing motion assist device.

FIG. 23 is an external view of a non-wearable standing motion assist device.

A non-wearable standing motion assist device 100A is an assist device of a type that is not worn by a user. Like the above-described exemplary embodiment, the standing motion assist device 100A includes a myoelectric potential measurement unit 101 and a body trunk posture measurement unit 102. In addition, the standing motion assist device 100A includes a fixed support unit 301, a frame unit 305, a seat unit 306, and a power unit 307. As illustrated in FIG. 23, the standing motion assist device 100A having such a configuration is mounted on a chair or is integrally attached to a chair.

The fixed support unit 301 is made of a metal or a hard resin material having a substantially L-shaped side cross section. The fixed support unit 301 is mounted on a floor, for example. The frame unit 305 is rotatably attached to the fixed support unit 301 via the power unit 307. The frame unit 305 is disposed on the seat of the chair. The seat unit 306 is attached to the frame unit 305 such that the buttocks of a user can be placed thereon. The power unit 307 rotates the frame unit 305 in a direction in which the knees of the user straighten. In the standing motion assist device 100A, by the rotation of the frame unit 305, the seat unit 306 uplifts the buttocks of the user and supports the user with the standing motion.

Even the standing motion assist device 100A having such a configuration can provide the same effect as the above-described exemplary embodiment.

In addition, according to the above-described exemplary embodiment, the chair identifying unit 107 acquires the measurement data measured during the sitting motion duration in order to identify the type of chair and identifies the type of chair on the basis of the acquired data. However, it is not necessary to acquire all of the data measured during the sitting motion duration. That is, the chair identifying unit 107 may identify the type of chair on the basis of the data measured in part of the sitting motion duration.

Furthermore, according to the above-described exemplary embodiment, the chair identifying unit 107 identifies the type of chair on the basis of the pattern expressed by the RMS of the myoelectric potential of each of the muscles, as illustrated in FIG. 11. However, the chair identifying unit 107 may identify the type of chair on the basis of the value of RMS of each of the myoelectric potential itself instead of the pattern.

Furthermore, according to the above-described exemplary embodiment, the chair identifying unit 107 identifies the type of chair in each of the sitting motion duration and the sitting duration. However, the chair type may be identified only in the sitting motion duration or the sitting duration.

According to the above-described exemplary embodiment and the modifications, each of the constituent elements may be configured by using dedicated hardware or execution of a software program suitable for the constituent element. Each of the constituent elements may be realized by a program execution unit, such as a central processing unit (CPU) or a processor, reading out and executing a software program recorded on a recording medium, such as a hard disk or a semiconductor memory. The software program for realizing the standing motion assist device according to the exemplary embodiment or each of the modifications is a program that causes a computer to perform the processing in steps included in the flowcharts illustrated in FIGS. 1B and FIGS. 3, 13, 16, 19, and 21.

In addition, according to the present disclosure, all or some of the units, apparatuses, members or parts, or all or some of the functional blocks in the block diagram illustrated in FIG. 1A or FIG. 2 may be configured by using a semiconductor device, a semiconductor integrated circuit (IC), or at least one electronic circuit including a large scale integration (LSI). The LSI or the IC may be integrated into one chip or may be formed by combining a plurality of chips. For example, functional blocks other than a memory element may be integrated into one chip. The terms "LSI" and "IC" are used herein, but the terms "system LSI", VLSI (very large scale integration), or ULSI (ultra large scale integration) may be used as well depending on the level of integration. Alternatively, a field programmable gate array (FPGA), which is programmable after fabrication of the LSI, or a reconfigurable logic device which allows reconfiguration of connections and settings of circuit cells in LSI may be used for the same purpose.

Furthermore, the functions or operations of all or some of the units, devices, and members or parts can be performed by software processing. In this case, the software is recorded on a non-transitory recording medium, such as one or a plurality of ROMs, optical disks, and hard disk drives. When the software is executed by a processor, the function identified by the software is performed by the processor and peripheral devices. The system or device may include one or more non-transitory recording media on which the software is recorded, a processor, and a required hardware device (e.g., an interface).

The standing motion assist device according to the present disclosure is useful for assisting a user with standing from a variety of types of chairs. The standing motion assist device is applicable to, for example, an assist suit or a robot.

What is claimed is:

1. A standing motion assist device comprising:
   a support mechanism attached to a leg of a user, the support mechanism supporting the user with motion;
   a sensor including at least one of a first sensor and a second sensor, the first sensor measuring posture information in accordance with postures of the user and outputting the posture information, the second sensor measuring myoelectric potential information including myoelectric potentials of the user and outputting the myoelectric potential information, the sensor outputting measurement data including at least one of the posture information and the myoelectric potential information;
   a memory that stores the measurement data; and
   a processor that controls the support mechanism by using the measurement data stored in the memory,
   wherein the processor detects a sitting motion of the user sitting in a chair on the basis of the measurement data,
   wherein the detection of the sitting motion includes a detection of a start of the sitting motion and a detection of an end of the sitting motion,
   wherein the processor identifies a type of the chair on the basis a first measurement data included in the measurement data and measured after the start of the sitting motion,
   wherein the processor detects a start of a standing motion of the user standing from the chair on the basis of second measurement data included in the measurement data and measured after the end of the sitting motion, and
   wherein the processor outputs assist information used to cause the support mechanism to assist the user with the standing motion in accordance with the identified type of the chair.

2. The standing motion assist device according to claim 1, wherein the myoelectric potential information includes first myoelectric potentials of a muscle included in muscles in the leg of the user.

3. The standing motion assist device according to claim 2,
   wherein the measurement data includes the first myoelectric potentials, and
   wherein the processor detects the start of the sitting motion if a myoelectric potential, included in the first myoelectric potentials, is greater than or equal to a threshold value corresponding to the muscle.

4. The standing motion assist device according to claim 1, wherein the posture information is at least one of accelerations, angular velocities, and geomagnetisms of an upper body of the user.

5. The standing motion assist device according to claim 4, wherein the measurement data includes the accelerations,
   wherein the processor calculates movement distances by which the upper body of the user moves in a vertical direction on the basis of the accelerations, and
   wherein if a movement distance, included in the movement distances, is greater than or equal to a threshold value, the processor detects the sitting motion.

6. The standing motion assist device according to claim 4, wherein the measurement data includes the accelerations,
   wherein the measurement data includes third measurement data and fourth measurement data measured later than the third measurement data, the third measurement data includes first accelerations, the fourth measurement data includes second accelerations, and the accelerations includes the first accelerations and the second accelerations, and
   wherein if a magnitude of a vertically downward component of an acceleration, included in the first accelerations, is greater than or equal to a first threshold value and a magnitude of a vertically upward component of an acceleration, included in the second acceleration, is greater than or equal o a second threshold value, the processor detects the sitting motion.

7. The standing motion assist device according to claim 1, wherein the posture information is angular velocities of an upper body of the user,
   wherein the measurement data includes the angular velocities,
   wherein the processor calculates trunk forward inclination angles of the user on the basis of the angular velocities, and
   wherein if myoelectric potentials, included in the myoelectric potentials, increases as time passes within a predetermined time period after a trunk forward inclination angle, included in the trunk forward inclination angles, reaches a value less than a threshold value, the processor detects the start of the sitting motion.

8. The standing motion assist device according to claim 1, wherein the processor identifies the type of the chair by using at least one of (i) data included in the measurement data and measured for a first duration during which the sitting motion is being performed and (ii) data included in the measurement data and measured for a second duration during which the user remains sitting.

9. The standing motion assist device according to claim 1, wherein the myoelectric potentials is myoelectric potentials of a muscle in a leg of the user,
   wherein the measurement data includes the myoelectric potentials of the muscle in the leg of the user, and
   wherein the processor identifies the type of the chair by determining whether the myoelectric potentials meet a condition which is defined for each of a plurality of types of chairs.

10. The standing motion assist device according to claim 1, wherein the posture information is accelerations of an upper body of the user,
    wherein the measurement data includes the accelerations, and
    wherein after the sitting motion starts, the processor calculates a movement distance by which the upper body of the user moves in a vertical direction on the basis of magnitudes of vertically upward components of the accelerations and identifies the type of the chair in accordance with the movement distance.

11. The standing motion assist device according to claim 1, wherein the posture information is accelerations of an upper body of the user,
    wherein the measurement data includes the accelerations, and
    wherein the processor calculates a maximum rate of change of accelerations in a vertical direction based on accelerations, included in the accelerations, during a predetermined time period from the start of the sitting motion and identifies the type of the chair in accordance with the maximum rate of change.

12. The standing motion assist device according to claim 1, wherein the posture information is angular velocities of an upper body of the user,
wherein the measurement data includes the angular velocities, and
wherein the processor calculates trunk forward inclination angles of the user by using first angular velocities, included in the angular velocities, for a duration during which the user is sitting after the sitting motion ends and identifies the type of the chair in accordance with the trunk forward inclination angles.

13. The standing motion assist device according to claim 1, wherein the second sensor includes two or more myoelectric potential measurement sensors, the two or more myoelectric potential measurement sensors measuring the myoelectric potentials of muscles in the leg of the user,
wherein the measurement data includes the myoelectric potentials, and
wherein the processor identifies an order in which the muscles start activities thereof on the basis of the myoelectric potentials and detects the start of the sitting motion if the identified order is the same as a predetermined order.

14. The standing motion assist device according to claim 13, wherein the posture information is angular velocities of the upper body of the user,
wherein the measurement data includes the angular velocities of the upper body of the user, and
wherein the processor calculates trunk forward inclination angles of the user based on the angular velocities and identifies the order after a trunk forward inclination angle, included in the trunk forward inclination angles, reaches a threshold value or less.

15. The standing motion assist device according to claim 14, wherein the processor updates the threshold value in accordance with the identified type of the chair.

16. The standing motion assist device according to claim 1, wherein the myoelectric potentials is myoelectric potentials of muscles in a leg of the user,
wherein the measurement data includes the myoelectric potentials, and
wherein the processor acquires an identification threshold value,
wherein the identification threshold value decreases with increasing height of a seat of the chair, and
wherein the processor detects the start of the standing motion if a myoelectric potential, included in the myoelectric potentials and measured after the sitting motion, reaches the identification threshold value or greater.

17. The standing motion assist device according to claim 1, wherein the processor outputs the assist information used to cause the support mechanism to change an angle of a knee joint of the user by using a force or a speed in accordance with the identified type of the chair.

18. A standing motion assist method comprising:
outputting measurement data including at least one of posture information and myoelectric potential information from a sensor including at least one of a first sensor and a second sensor, the first sensor measuring the posture information in accordance with postures of a user and outputting the posture information, the second sensor measuring the myoelectric potential information including myoelectric potentials of the user and outputting the myoelectric potential information;
storing the measurement data in a memory; and
controlling a support mechanism that is attached to a leg of the user and that assists the user with motion by using a processor referencing the measurement data stored in the memory,
wherein the processor detects a sitting motion of the user sitting in a chair on the basis of the measurement data,
wherein the detection of the sitting motion includes a detection of a start of the sitting motion and a detection of an end of the sitting motion,
wherein the processor identifies a type of the chair on the basis of first measurement data included in the measurement data and measured after the start of the sitting motion,
wherein the processor detects a start of a standing motion of the user standing from the chair on the basis of second measurement data included in the measurement data and measured after the end of the sitting motion, and
wherein the processor outputs assist information used to cause the support mechanism to assist the user with the standing motion in accordance with the identified type of the chair.

19. A non-transitory computer-readable recording medium storing a control program that causes a device including a processor to perform a process, the process comprising:
receiving measurement data including at least one of posture information and myoelectric potential information from a sensor including at least one of a first sensor and a second sensor, the first sensor measuring the posture information in accordance with postures of the user and outputting the posture information, the second sensor measuring the myoelectric potential information including myoelectric potentials of the user and outputting the myoelectric potential information;
storing the measurement data in a memory;
controlling a support mechanism that is attached to a leg of the user and that assists the user with motion by using the measurement data stored in the memory;
detecting a sitting motion of the user sitting in a chair on the basis of the measurement data, the detection of the sitting motion including a detection of a start of the sitting motion and a detection of an end of the sitting motion,
identifying a type of the chair on the basis of a first measurement data included in the measurement data and measured after the start of the sitting motion;
detecting a start of a standing motion of the user standing from the chair on the basis of second measurement data included in the measurement data and measured after the end of the sitting motion; and
outputting assist information used to cause the support mechanism to assist the user with the standing motion in accordance with the identified type of the chair.

* * * * *